United States Patent [19]
Ichijo et al.

[11] Patent Number: 5,968,752
[45] Date of Patent: Oct. 19, 1999

[54] METHOD FOR IDENTIFYING AN OP-1 ANALOG WHICH BINDS AN ALK-1 RECEPTOR

[75] Inventors: Hidenori Ichijo, Tokyo; Hideki Nishitoh, Kanagawa-ken, both of Japan; Kuber T. Sampath, Medway, Mass.

[73] Assignees: Creative BioMolecules, Inc., Hopkinton, Mass.; The Ludwig Institute for Cancer Research, New York, N.Y.

[21] Appl. No.: 08/696,268

[22] Filed: Aug. 13, 1996

Related U.S. Application Data

[60] Provisional application No. 60/002,313, Aug. 14, 1995.

[51] Int. Cl.[6] .................... G01N 33/566; C07K 14/71; C07K 14/705
[52] U.S. Cl. .................... 435/7.2; 435/7.1; 530/350
[58] Field of Search .................... 435/7.1, 7.2, 69.1; 436/501; 530/300, 350

[56] References Cited

U.S. PATENT DOCUMENTS

| | | | |
|---|---|---|---|
| 5,141,905 | 8/1992 | Rosen et al. | 435/69.1 |
| 5,538,892 | 7/1996 | Donahoe | 435/240.2 |
| 5,620,867 | 4/1997 | Kiefer et al. | 435/69.4 |
| 5,650,276 | 7/1997 | Smart et al. | 435/6 |

FOREIGN PATENT DOCUMENTS

| | | |
|---|---|---|
| 92/07073 | 10/1991 | WIPO . |
| 92/20793 | 5/1992 | WIPO . |
| 93/05172 | 3/1993 | WIPO . |
| 93/19177 | 9/1993 | WIPO . |
| 94/06399 | 9/1993 | WIPO . |
| 94/11502 | 5/1994 | WIPO . |
| 95/07982 | 3/1995 | WIPO . |
| 95/30003 | 4/1995 | WIPO . |
| 95/14778 | 6/1995 | WIPO . |
| 96/14412 | 5/1996 | WIPO . |
| 96/14579 | 5/1996 | WIPO . |
| 96/18735 | 6/1996 | WIPO . |

OTHER PUBLICATIONS

Strader et al., Structural basis of beta–adrenergic receptor function, FASEB J., 3: 1825–1832, 1989.

Andrews et al., Inhibition of proliferation and induction of differentiation of pluripotnent human enbryonal carcinoma cells by osteogenic protein–1 (or bone morphogenic protein–7), Lab. Invest., 71(2): 243–251, Aug. 1994.

Gibbs, W., More fun than root canal, Scientifici American, 269(5): 106, Nov. 1993.

Yamashita et al., Ostogenic protein–1 binds to activin tupell receptors and induces certain activin–like effects, J. Cell Biol., 130(1): 217–226, Jul. 1995.

Attisano et al. (1993), "Identification of Human Activin & TGF–β . . . with Type II Receptors," *Cell* 75:671–680.

Bassing et al. (1994), "A Transforming Growth Factor β Type I Receptor . . . Gene Expression," *Science* 263:87–89.

Inagaki et al. (1993), "Growth Inhibition by Transforming Growth Factor β Type I . . . TGF–β Receptor Type II cDNA," *Proc. Natl. Acad. Sci. USA* 90:5359–5363.

Paralkar et al. (1991), "Identification and Characterization of Cellular Binding Proteins . . . Bone Differentiation Cascade," *Proc. Natl. Acad. Sci. USA* 88:3397–3401.

Tsuchida et al., "Cloning and Characterization of a Transmembrane Serine Kinase . . . Type I Receptor," *Proc. Natl. Acad. Sci. USA* 90:11242–11246 (1993).

He et al., "Developmental Expression of Four Novel Serine/Threonine Kinase . . . Type II Receptor Family," *Development Dynamics* 196:133–142 (1993).

Matsuzaki et al., "A Widely Expressed Transmembrane Serine/Threonine Kinase . . . Bone Morphogenic Factor," *J. Bio. Chem.* 268:12719–12722 (1993).

Estevez et al., "The daf–4 Gene Encodes a Bone Morphogenetic . . . Dauer Larva Development," *Nature* 365:644–649 (1993).

Franzen et al., "Cloning of a TGF–β Type I Receptor That Forms a Heteromeric Complex with the TGF–β Type II Receptor," *Cell* 75:681–692 (1993).

Massague, "Receptors for the TGF–β Family," *Cell* 69:1067–1070 (1992).

Wrana et al., "TGF–β Signals Through a Heteromeric Protein Kinase Receptor Complet," *Cell* 71:1003–1014 (1992).

Childs et al., "Identification of a Drosophila Activin Receptor," *Proc. Natl. Acad. Sci. USA* 90:9475–9479 (1993).

Mathews et al., "Cloning of a Second Type of Activin Receptor and Functional Characterization in Xenopus Embryos," *Science* 255:1702–1705 (1992).

Ebner et al., "Determination of Type I Receptor Specificity by the Type II Receptors for TGF–β or Activin," *Science* 262:900–902 (1993).

Ebner et al., "Cloning of a Type I TGF–β Receptor and Its Effect on TGF–β Binding to the Type II Receptor," *Science* 260:1344–1348 (1993).

ten Dijke et al., "Characterization of Type I Receptors for Transforming Growth Factor–β and Activin," *Science* 264:101–103 (1994).

(List continued on next page.)

*Primary Examiner*—Lila Feisee
*Assistant Examiner*—Claire M. Kaufman
*Attorney, Agent, or Firm*—Testa, Hurwitz & Thibeault, LLP

[57] ABSTRACT

Disclosed are (1) nucleic acid sequences, amino acid sequences, homologies, structural features, and various other data characterizing morphogen cell surface receptors, particularly OP-1-binding cell surface receptors, e.g., ALK-1; (2) methods for producing receptor proteins, including fragments thereof, using recombinant DNA technology; (3) methods for identifying novel morphogen receptors and their encoding DNAs; (4) methods for identifying compounds capable of modulating endogenous morphogen receptor levels; and (5) methods and compositions for identifying and producing morphogen analogs useful in the design of morphogen agonists and antagonists for therapeutic, diagnostic, and experimental uses.

3 Claims, 2 Drawing Sheets

OTHER PUBLICATIONS

Lin et al., "Receptors for the TGF-β Superfamily: Multiple Polypeptides and Serine/Threonine Kinases," *Cell* 3:14–25 (1993).

ten Dijke et al. (1993), "Activin Receptor–Like Kinases; A Novel Subclass of Cell Surface Receptors with Predicted Serine/Threonine Kinase Activity," *Oncogene* 8:2879–2887.

Yamaji et al. (1993), "The molecular cloning of bone morphogenic protein receptors," *Journal of Bone & Mineral Research* 8:S145.

Vukicevic et al. (1994), "Localization of Osteogenic Protein–1 (Bone Morphogenetic Protein–7) During Human Embryonic Development: High Affinity Binding to Basement Membranes," *B.B.R.C.* 198:693–700.

Koenig et al. (1994), "Characterization and Cloning of a Receptor for BMP–2 and BMP–4 from NIH 3T3 Cells," *Mol Cell Biol* 14:5961–5974.

ten Dijke et al. (1994), "Identification of Type I Receptors for Osteogenic Protein–1 and Bone Morphogenetic Protein–4," *J. Biol Chem* 269:16985–16988.

Kawabata et al. (1995), "Cloning of a Novel Type II Serine/Threonine Kinase Receptor through Interaction with the Type I Transforming Growth Factor–β Receptor," *J. Biol Chem* 270:5625–5630.

Rosenzweig et al. (1995), "Cloning and characterization of a human type II receptor for bone morphogenetic proteins," *Proc. Natl. Acad. Sci.*, 92:7632–7636.

Ishikawa et al. (1995), "Truncated Type II Receptor for BMP–4 Induces Secondary Axial Structures in Xenopus Embryos," *Biochemical and Biophysical Research Communications*, 216:26–33.

| cDNA | ALK-1 | | | | ALK-3 | | | | ALK-5 | | | |
|---|---|---|---|---|---|---|---|---|---|---|---|---|
| ZnCl₂ | − | | | + | − | | | + | − | | | + |
| ligand | − | O | Oβ | A | − | O | Oβ | A | − | O | Oβ | A |
| PAI-1 → | | | | | | | | | | | | |

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1509 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1509
      (D) OTHER INFORMATION: /product= "Human ALK-1"

(xi) SEQUENCE DESCRIPTION: SEQ ID NO:1:

```
ATG ACC TTG GGC TCC CCC AGG AAA GGC CTT CTG ATG CTG CTG ATG GCC     48
Met Thr Leu Gly Ser Pro Arg Lys Gly Leu Leu Met Leu Leu Met Ala
 1               5                  10                  15

TTG GTG ACC CAG GGA GAC CCT GTG AAG CCG TCT CGG GGC CCG CTG GTG     96
Leu Val Thr Gln Gly Asp Pro Val Lys Pro Ser Arg Gly Pro Leu Val
                 20                  25                  30

ACC TGC ACG TGT GAG AGC CCA CAT TGC AAG GGG CCT ACC TGC CGG GGG    144
Thr Cys Thr Cys Glu Ser Pro His Cys Lys Gly Pro Thr Cys Arg Gly
             35                  40                  45

GCC TGG TGC ACA GTA GTG CTG GTG CGG GAG GAG GGG AGG CAC CCC CAG    192
Ala Trp Cys Thr Val Val Leu Val Arg Glu Glu Gly Arg His Pro Gln
 50                  55                  60

GAA CAT CGG GGC TGC GGG AAC TTG CAC AGG GAG CTC TGC AGG GGG CGC    240
Glu His Arg Gly Cys Gly Asn Leu His Arg Glu Leu Cys Arg Gly Arg
 65                  70                  75                  80

CCC ACC GAG TTC GTC AAC CAC TAC TGC TGC GAC AGC CAC CTC TGC AAC    288
Pro Thr Glu Phe Val Asn His Tyr Cys Cys Asp Ser His Leu Cys Asn
                 85                  90                  95

CAC AAC GTG TCC CTG GTG CTG GAG GCC ACC CAA CCT CCT TCG GAG CAG    336
His Asn Val Ser Leu Val Leu Glu Ala Thr Gln Pro Pro Ser Glu Gln
                100                 105                 110

CCG GGA ACA GAT GGC CAG CTG GCC CTG ATC CTG GGC CCC GTG CTG GCC    384
Pro Gly Thr Asp Gly Gln Leu Ala Leu Ile Leu Gly Pro Val Leu Ala
            115                 120                 125

TTG CTG GCC CTG GTG GCC CTG GGT GTC CTG GGC CTG TGG CAT GTC CGA    432
Leu Leu Ala Leu Val Ala Leu Gly Val Leu Gly Leu Trp His Val Arg
        130                 135                 140

CGG AGG CAG GAG AAG CAG CGT GGC CTG CAC AGC GAG CTG GGA GAG TCC    480
Arg Arg Gln Glu Lys Gln Arg Gly Leu His Ser Glu Leu Gly Glu Ser
145                 150                 155                 160

AGT CTC ATC CTG AAA GCA TCT GAG CAG GGC GAC ACG ATG TTG GGG GAC    528
Ser Leu Ile Leu Lys Ala Ser Glu Gln Gly Asp Thr Met Leu Gly Asp
                165                 170                 175

CTC CTG GAC AGT GAC TGC ACC ACA GGG AGT GGC TCA GGG CTC CCC TTC    576
Leu Leu Asp Ser Asp Cys Thr Thr Gly Ser Gly Ser Gly Leu Pro Phe
            180                 185                 190

CTG GTG CAG AGG ACA GTG GCA CGG CAG GTT GCC TTG GTG GAG TGT GTG    624
Leu Val Gln Arg Thr Val Ala Arg Gln Val Ala Leu Val Glu Cys Val
        195                 200                 205

GGA AAA GGC CGC TAT GGC GAA GTG TGG CGG GGC TTG TGG CAC GGT GAG    672
Gly Lys Gly Arg Tyr Gly Glu Val Trp Arg Gly Leu Trp His Gly Glu
    210                 215                 220

AGT GTG GCC GTC AAG ATC TTC TCC TCG AGG GAT GAA CAG TCC TGG TTC    720
Ser Val Ala Val Lys Ile Phe Ser Ser Arg Asp Glu Gln Ser Trp Phe
225                 230                 235                 240

CGG GAG ACT GAG ATC TAT AAC ACA GTA TTG CTC AGA CAC GAC AAC ATC    768
Arg Glu Thr Glu Ile Tyr Asn Thr Val Leu Leu Arg His Asp Asn Ile
                245                 250                 255

CTA GGC TTC ATC GCC TCA GAC ATG ACC TCC CGC AAC TCG AGC ACG CAG    816
Leu Gly Phe Ile Ala Ser Asp Met Thr Ser Arg Asn Ser Ser Thr Gln
            260                 265                 270

CTG TGG CTC ATC ACG CAC TAC CAC GAG CAC GGC TCC CTC TAC GAC TTT    864
Leu Trp Leu Ile Thr His Tyr His Glu His Gly Ser Leu Tyr Asp Phe
        275                 280                 285

CTG CAG AGA CAG ACG CTG GAG CCC CAT CTG GCT CTG AGG CTA GCT GTG    912
Leu Gln Arg Gln Thr Leu Glu Pro His Leu Ala Leu Arg Leu Ala Val
    290                 295                 300

TCC GCG GCA TGC GGC CTG GCG CAC CTG CAC GTG GAG ATC TTC GGT ACA    960
```

```
Ser Ala Ala Cys Gly Leu Ala His Leu His Val Glu Ile Phe Gly Thr
305                 310                 315                 320

CAG GGC AAA CCA GCC ATT GCC CAC CGC GAC TTC AAG AGC CGC AAT GTG      1008
Gln Gly Lys Pro Ala Ile Ala His Arg Asp Phe Lys Ser Arg Asn Val
                325                 330                 335

CTG GTC AAG AGC AAC CTG CAG TGT TGC ATC GCC GAC CTG GGC CTG GCT      1056
Leu Val Lys Ser Asn Leu Gln Cys Cys Ile Ala Asp Leu Gly Leu Ala
                340                 345                 350

GTG ATG CAC TCA CAG GGC AGC GAT TAC CTG GAC ATC GGC AAC AAC CCG      1104
Val Met His Ser Gln Gly Ser Asp Tyr Leu Asp Ile Gly Asn Asn Pro
                355                 360                 365

AGA GTG GGC ACC AAG CGG TAC ATG GCA CCC GAG GTG CTG GAC GAG CAG      1152
Arg Val Gly Thr Lys Arg Tyr Met Ala Pro Glu Val Leu Asp Glu Gln
    370                 375                 380

ATC CGC ACG GAC TGC TTT GAG TCC TAC AAG TGG ACT GAC ATC TGG GCC      1200
Ile Arg Thr Asp Cys Phe Glu Ser Tyr Lys Trp Thr Asp Ile Trp Ala
385                 390                 395                 400

TTT GGC CTG GTG CTG TGG GAG ATT GCC CGC CGG ACC ATC GTG AAT GGC      1248
Phe Gly Leu Val Leu Trp Glu Ile Ala Arg Arg Thr Ile Val Asn Gly
                405                 410                 415

ATC GTG GAG GAC TAT AGA CCA CCC TTC TAT GAT GTG GTG CCC AAT GAC      1296
Ile Val Glu Asp Tyr Arg Pro Pro Phe Tyr Asp Val Val Pro Asn Asp
                420                 425                 430

CCC AGC TTT GAG GAC ATG AAG AAG GTG GTG TGT GTG GAT CAG CAG ACC      1344
Pro Ser Phe Glu Asp Met Lys Lys Val Val Cys Val Asp Gln Gln Thr
                435                 440                 445

CCC ACC ATC CCT AAC CGG CTG GCT GCA GAC CCG GTC CTC TCA GGC CTA      1392
Pro Thr Ile Pro Asn Arg Leu Ala Ala Asp Pro Val Leu Ser Gly Leu
    450                 455                 460

GCT CAG ATG ATG CGG GAG TGC TGG TAC CCA AAC CCC TCT GCC CGA CTC      1440
Ala Gln Met Met Arg Glu Cys Trp Tyr Pro Asn Pro Ser Ala Arg Leu
465                 470                 475                 480

ACC GCG CTG CGG ATC AAG AAG ACA CTA CAA AAA ATT AGC AAC AGT CCA      1488
Thr Ala Leu Arg Ile Lys Lys Thr Leu Gln Lys Ile Ser Asn Ser Pro
                485                 490                 495

GAG AAG CCT AAA GTG ATT CAA                                          1509
Glu Lys Pro Lys Val Ile Gln
                500

(2) INFORMATION FOR SEQ ID NO:2:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Leu Gly Ser Pro Arg Lys Gly Leu Leu Met Leu Leu Met Ala
1               5                   10                  15

Leu Val Thr Gln Gly Asp Pro Val Lys Pro Ser Arg Gly Pro Leu Val
                20                  25                  30

Thr Cys Thr Cys Glu Ser Pro His Cys Lys Gly Pro Thr Cys Arg Gly
            35                  40                  45

Ala Trp Cys Thr Val Val Leu Val Arg Glu Glu Gly Arg His Pro Gln
        50                  55                  60

Glu His Arg Gly Cys Gly Asn Leu His Arg Glu Leu Cys Arg Gly Arg
65                  70                  75                  80

Pro Thr Glu Phe Val Asn His Tyr Cys Cys Asp Ser His Leu Cys Asn
                85                  90                  95
```

```
His Asn Val Ser Leu Val Leu Glu Ala Thr Gln Pro Pro Ser Glu Gln
            100                 105                 110

Pro Gly Thr Asp Gly Gln Leu Ala Leu Ile Leu Gly Pro Val Leu Ala
            115                 120                 125

Leu Leu Ala Leu Val Ala Leu Gly Val Leu Gly Leu Trp His Val Arg
130                 135                 140

Arg Arg Gln Glu Lys Gln Arg Gly Leu His Ser Glu Leu Gly Glu Ser
145                 150                 155                 160

Ser Leu Ile Leu Lys Ala Ser Glu Gln Gly Asp Thr Met Leu Gly Asp
                    165                 170                 175

Leu Leu Asp Ser Asp Cys Thr Thr Gly Ser Gly Ser Gly Leu Pro Phe
                    180                 185                 190

Leu Val Gln Arg Thr Val Ala Arg Gln Val Ala Leu Glu Cys Val
                    195                 200                 205

Gly Lys Gly Arg Tyr Gly Glu Val Trp Arg Gly Leu Trp His Gly Glu
210                 215                 220

Ser Val Ala Val Lys Ile Phe Ser Ser Arg Asp Glu Gln Ser Trp Phe
225                 230                 235                 240

Arg Glu Thr Glu Ile Tyr Asn Thr Val Leu Leu Arg His Asp Asn Ile
                    245                 250                 255

Leu Gly Phe Ile Ala Ser Asp Met Thr Ser Arg Asn Ser Ser Thr Gln
                    260                 265                 270

Leu Trp Leu Ile Thr His Tyr His Glu His Gly Ser Leu Tyr Asp Phe
            275                 280                 285

Leu Gln Arg Gln Thr Leu Glu Pro His Leu Ala Leu Arg Leu Ala Val
            290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val
                    325                 330                 335

Leu Val Lys Ser Asn Leu Gln Cys Cys Ile Ala Asp Leu Gly Leu Ala
                    340                 345                 350

Val Met His Ser Gln Gly Ser Asp Tyr Leu Asp Ile Gly Asn Asn Pro
            355                 360                 365

Arg Val Gly Thr Lys Arg Tyr Met Ala Pro Glu Val Leu Asp Glu Gln
            370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
                    405                 410                 415

Ile Val Glu Asp Tyr Arg Pro Pro Phe Tyr Asp Val Val Pro Asn Asp
                    420                 425                 430

Pro Ser Phe Glu Asp Met Lys Lys Val Val Cys Val Asp Gln Gln Thr
            435                 440                 445

Pro Thr Ile Pro Asn Arg Leu Ala Ala Asp Pro Val Leu Ser Gly Leu
            450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
                    485                 490                 495

Glu Lys Pro Lys Val Ile Gln
            500
```

(2) INFORMATION FOR SEQ ID NO:3:

(i) SEQUENCE CHARACTERISTICS:
        (A) LENGTH: 1822 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 49..1341
        (D) OTHER INFORMATION: /function= "Osteogenic Protein"
            /product= "OP1"
            /standard_name= "OP1"

(xi) SEQUENCE DESCRIPTION: SEQ ID NO:3:

```
GGTGCGGGCC CGGAGCCCGG AGCCCGGGTA GCGCGTAGAG CCGGCGCG ATG CAC GTG         57
                                                     Met His Val
                                                       1

CGC TCA CTG CGA GCT GCG GCG CCG CAC AGC TTC GTG GCG CTC TGG GCA        105
Arg Ser Leu Arg Ala Ala Ala Pro His Ser Phe Val Ala Leu Trp Ala
      5                  10                  15

CCC CTG TTC CTG CTG CGC TCC GCC CTG GCC GAC TTC AGC CTG GAC AAC        153
Pro Leu Phe Leu Leu Arg Ser Ala Leu Ala Asp Phe Ser Leu Asp Asn
 20                  25                  30                  35

GAG GTG CAC TCG AGC TTC ATC CAC CGG CGC CTC CGC AGC CAG GAG CGG        201
Glu Val His Ser Ser Phe Ile His Arg Arg Leu Arg Ser Gln Glu Arg
              40                  45                  50

CGG GAG ATG CAG CGC GAG ATC CTC TCC ATT TTG GGC TTG CCC CAC CGC        249
Arg Glu Met Gln Arg Glu Ile Leu Ser Ile Leu Gly Leu Pro His Arg
         55                  60                  65

CCG CGC CCG CAC CTC CAG GGC AAG CAC AAC TCG GCA CCC ATG TTC ATG        297
Pro Arg Pro His Leu Gln Gly Lys His Asn Ser Ala Pro Met Phe Met
 70                  75                  80

CTG GAC CTG TAC AAC GCC ATG GCG GTG GAG GAG GGC GGC GGG CCC GGC        345
Leu Asp Leu Tyr Asn Ala Met Ala Val Glu Glu Gly Gly Gly Pro Gly
     85                  90                  95

GGC CAG GGC TTC TCC TAC CCC TAC AAG GCC GTC TTC AGT ACC CAG GGC        393
Gly Gln Gly Phe Ser Tyr Pro Tyr Lys Ala Val Phe Ser Thr Gln Gly
100                 105                 110                 115

CCC CCT CTG GCC AGC CTG CAA GAT AGC CAT TTC CTC ACC GAC GCC GAC        441
Pro Pro Leu Ala Ser Leu Gln Asp Ser His Phe Leu Thr Asp Ala Asp
                120                 125                 130

ATG GTC ATG AGC TTC GTC AAC CTC GTG GAA CAT GAC AAG GAA TTC TTC        489
Met Val Met Ser Phe Val Asn Leu Val Glu His Asp Lys Glu Phe Phe
            135                 140                 145

CAC CCA CGC TAC CAC CAT CGA GAG TTC CGG TTT GAT CTT TCC AAG ATC        537
His Pro Arg Tyr His His Arg Glu Phe Arg Phe Asp Leu Ser Lys Ile
        150                 155                 160

CCA GAA GGG GAA GCT GTC ACG GCA GCC GAA TTC CGG ATC TAC AAG GAC        585
Pro Glu Gly Glu Ala Val Thr Ala Ala Glu Phe Arg Ile Tyr Lys Asp
165                 170                 175

TAC ATC CGG GAA CGC TTC GAC AAT GAG ACG TTC CGG ATC AGC GTT TAT        633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC        681
Gln Val Leu Gln Glu His Leu Gly Arg Glu Ser Asp Leu Phe Leu Leu
                200                 205                 210

GAC AGC CGT ACC CTC TGG GCC TCG GAG GAG GGC TGG CTG GTG TTT GAC        729
Asp Ser Arg Thr Leu Trp Ala Ser Glu Glu Gly Trp Leu Val Phe Asp
            215                 220                 225
```

```
ATC ACA GCC ACC AGC AAC CAC TGG GTG GTC AAT CCG CGG CAC AAC CTG      777
Ile Thr Ala Thr Ser Asn His Trp Val Val Asn Pro Arg His Asn Leu
            230                 235                 240

GGC CTG CAG CTC TCG GTG GAG ACG CTG GAT GGG CAG AGC ATC AAC CCC      825
Gly Leu Gln Leu Ser Val Glu Thr Leu Asp Gly Gln Ser Ile Asn Pro
245                 250                 255

AAG TTG GCG GGC CTG ATT GGG CGG CAC GGG CCC CAG AAC AAG CAG CCC      873
Lys Leu Ala Gly Leu Ile Gly Arg His Gly Pro Gln Asn Lys Gln Pro
260                 265                 270                 275

TTC ATG GTG GCT TTC TTC AAG GCC ACG GAG GTC CAC TTC CGC AGC ATC      921
Phe Met Val Ala Phe Phe Lys Ala Thr Glu Val His Phe Arg Ser Ile
                280                 285                 290

CGG TCC ACG GGG AGC AAA CAG CGC AGC CAG AAC CGC TCC AAG ACG CCC      969
Arg Ser Thr Gly Ser Lys Gln Arg Ser Gln Asn Arg Ser Lys Thr Pro
        295                 300                 305

AAG AAC CAG GAA GCC CTG CGG ATG GCC AAC GTG GCA GAG AAC AGC AGC     1017
Lys Asn Gln Glu Ala Leu Arg Met Ala Asn Val Ala Glu Asn Ser Ser
310                 315                 320

AGC GAC CAG AGG CAG GCC TGT AAG AAG CAC GAG CTG TAT GTC AGC TTC     1065
Ser Asp Gln Arg Gln Ala Cys Lys Lys His Glu Leu Tyr Val Ser Phe
325                 330                 335

CGA GAC CTG GGC TGG CAG GAC TGG ATC ATC GCG CCT GAA GGC TAC GCC     1113
Arg Asp Leu Gly Trp Gln Asp Trp Ile Ile Ala Pro Glu Gly Tyr Ala
340                 345                 350                 355

GCC TAC TAC TGT GAG GGG GAG TGT GCC TTC CCT CTG AAC TCC TAC ATG     1161
Ala Tyr Tyr Cys Glu Gly Glu Cys Ala Phe Pro Leu Asn Ser Tyr Met
                360                 365                 370

AAC GCC ACC AAC CAC GCC ATC GTG CAG ACG CTG GTC CAC TTC ATC AAC     1209
Asn Ala Thr Asn His Ala Ile Val Gln Thr Leu Val His Phe Ile Asn
        375                 380                 385

CCG GAA ACG GTG CCC AAG CCC TGC TGT GCG CCC ACG CAG CTC AAT GCC     1257
Pro Glu Thr Val Pro Lys Pro Cys Cys Ala Pro Thr Gln Leu Asn Ala
390                 395                 400

ATC TCC GTC CTC TAC TTC GAT GAC AGC TCC AAC GTC ATC CTG AAG AAA     1305
Ile Ser Val Leu Tyr Phe Asp Asp Ser Ser Asn Val Ile Leu Lys Lys
405                 410                 415

TAC AGA AAC ATG GTG GTC CGG GCC TGT GGC TGC CAC TAGCTCCTCC          1351
Tyr Arg Asn Met Val Val Arg Ala Cys Gly Cys His
420                 425                 430

GAGAATTCAG ACCCTTTGGG GCCAAGTTTT TCTGGATCCT CCATTGCTCG CCTTGGCCAG   1411

GAACCAGCAG ACCAACTGCC TTTTGTGAGA CCTTCCCCTC CCTATCCCCA ACTTTAAAGG   1471

TGTGAGAGTA TTAGGAAACA TGAGCAGCAT ATGGCTTTTG ATCAGTTTTT CAGTGGCAGC   1531

ATCCAATGAA CAAGATCCTA CAAGCTGTGC AGGCAAAACC TAGCAGGAAA AAAAACAAC    1591

GCATAAAGAA AAATGGCCGG GCCAGGTCAT TGGCTGGGAA GTCTCAGCCA TGCACGGACT   1651

CGTTTCCAGA GGTAATTATG AGCGCCTACC AGCCAGGCCA CCCAGCCGTG GGAGGAAGGG   1711

GGCGTGGCAA GGGGTGGGCA CATTGGTGTC TGTGCGAAAG GAAAATTGAC CCGGAAGTTC   1771

CTGTAATAAA TGTCACAATA AAACGAATGA ATGAAAAAAA AAAAAAAAA A             1822
```

(2) INFORMATION FOR SEQ ID NO:4:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:4:

-continued

```
Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
             35                  40                  45

Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
             85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
            370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430
```

(2) INFORMATION FOR SEQ ID NO:5:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= OPX
            /note= "Each Xaa is independently selected from a group of one
            or more specified amino acids as defined in the Specification."

(xi) SEQUENCE DESCRIPTION: SEQ ID NO:5:

```
Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Xaa Leu Xaa Lys Xaa Arg Asn Met Val Val
                85                  90                  95

Xaa Ala Cys Gly Cys His
            100
```

(2) INFORMATION FOR SEQ ID NO:6:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:6:

```
Gly Xaa Gly Xaa Xaa Gly
1               5
```

(2) INFORMATION FOR SEQ ID NO:7:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:7:

```
His Arg Asp Leu Lys Ser Lys Asn
1               5
```

(2) INFORMATION FOR SEQ ID NO:8:

(i) SEQUENCE CHARACTERISTICS:
(A) LENGTH: 9 amino acids
(B) TYPE: amino acid

-continued

```
    (C) STRANDEDNESS:
    (D) TOPOLOGY: linear (ii) MOLECULE TYPE: peptide (xi) SEQUENCE DESCRIPTION: SEQ ID NO:8:

Gly Thr Lys Arg Tyr Met Ala Pro Glu
1               5
```

METHOD FOR IDENTIFYING AN OP-1 ANALOG WHICH BINDS AN ALK-1 RECEPTOR

RELATED APPLICATIONS

The present invention claims priority to Provisional Application U.S. Ser. No. 60/002,313 filed Aug. 14, 1995, the entire disclosure of which is incorporated herein by reference.

FIELD OF THE INVENTION

This invention relates generally to the field of tissue morphogenesis and more particularly to morphogenic protein-specific cell surface receptors.

BACKGROUND OF THE INVENTION

Cell differentiation is the central characteristic of tissue morphogenesis which initiates during embryogenesis, and continues to various degrees throughout the life of an organism in adult tissue repair and regeneration mechanisms. The degree of morphogenesis in adult tissue varies among different tissues and is related, among other things, to the degree of cell turnover in a given tissue.

The cellular and molecular events which govern the stimulus for differentiation of cells is an area of intensive research. In the medical and veterinary fields, it is anticipated that the discovery of the factor or factors which control cell differentiation and tissue morphogenesis will advance significantly medicine's ability to repair and regenerate diseased or damaged mammalian tissues and organs. Particularly useful areas for human and veterinary therapeutics include reconstructive surgery and in the treatment of tissue degenerative diseases including arthritis, emphysema, osteoporosis, cardiomyopathy, cirrhosis, degenerative nerve diseases, inflammatory diseases, and cancer, and in the regeneration of tissues, organs and limbs. (In this and related applications, the terms "morphogenetic" and "morphogenic" are used interchangeably.)

A number of different factors have been isolated in recent years which appear to play a role in cell differentiation. Recently, a distinct subfamily of the "superfamily" of structurally related proteins referred to in the art as the "transforming growth factor-β (TGF-β) superfamily of proteins" have been identified as true tissue morphogens.

The members of this distinct "subfamily" of true tissue morphogenic proteins share substantial amino acid sequence homology within their morphogenically active C-terminal domains (at least 50% identity in the C-terminal 102 amino acid sequence), including a conserved six or seven cysteine skeleton, and share the in vivo activity of inducing tissue-specific morphogenesis in a variety of organs and tissues. The proteins apparently contact and interact with progenitor cells e.g., by binding suitable cell surface molecules, predisposing or otherwise stimulating the cells to proliferate and differentiate in a morphogenically permissive environment. These morphogenic proteins are capable of inducing the developmental cascade of cellular and molecular events that culminate in the formation of new organ-specific tissue, including any vascularization, connective tissue formation, and nerve innervation as required by the naturally occurring tissue. The proteins have been shown to induce morphogenesis of both bone cartilage and bone, as well as periodontal tissues, dentin, liver, and neural tissue, including retinal tissue.

The true tissue morphogenic proteins identified to date include proteins originally identified as bone inductive proteins. These include OP-1, (osteogenic protein-1, also referred to in related applications as "OP1"), its Drosophila homolog, 60A, with which it shares 69% identity in the C-terminal "seven cysteine" domain, and the related proteins OP-2 (also referred to in related applications as "OP2") and OP-3, both of which share approximately 70–75% identity with OP-1 in the C-terminal seven cysteine domain, as well as BMP-5, BMP-6 and its murine homolog, Vgr-1, all of which share greater than 85% identity with OP-1 in the C-terminal seven cysteine domain, and the BMP-6 Xenopus homolog, Vg1, which shares approximately 57% identity with OP-1 in the C-terminal seven cysteine domain. Other bone inductive proteins include the CBMP-2 proteins (also referred to in the art as BMP-2 and BMP-4) and their Drosophila homolog, dpp. Another tissue morphogenic protein is GDF-1 (from mouse). See, for example, PCT documents US92/01968 and US92/07358, the disclosures of which are incorporated herein by reference. Other proteins identified in the art as bone morphogenic proteins include BMP-9 (See PCT/US92/05374; WO 93/00432); BMP-10 (PCT/US94/05288; WO 94/26893); BMP-11 (PCT/US94/05290; WO 94/26892); and BMP-12 and BMP-13 (PCT/US94/14030; WO 95/16035).

As stated above, these true tissue morphogenic proteins are recognized in the art as a distinct subfamily of proteins different from other members of the TGF-β superfamily in that they share a high degree of sequence identity in the C-terminal domain and in that the true tissue morphogenic proteins are able to induce, on their own, the full cascade of events that result in formation of functional tissue rather than merely inducing formation of fibrotic (scar) tissue. Specifically, members of the family of morphogenic proteins are capable of all of the following in a morphogenically permissive environment: stimulating cell proliferation and cell differentiation, and supporting the growth and maintenance of differentiated cells. The morphogenic proteins apparently may act as endocrine, paracrine or autocrine factors.

The morphogenic proteins are capable of significant species "crosstalk." That is, xenogenic (foreign species) homologs of these proteins can substitute for one another in functional activity. For example, dpp and 60A, two Drosophila proteins, can substitute for their mammalian homologs, BMP-2/4 and OP-1, respectively, and induce endochondral bone formation at a non-bony site in a standard rat bone formation assay. Similarly, BMP-2 has been shown to rescue a dpp- mutation in Drosophila. In their native form, however, the proteins appear to be tissue-specific, each protein typically being expressed in or provided to one or only a few tissues or, alternatively, expressed only at particular times during development. For example, GDF-1 appears to be expressed primarily in neural tissue, while OP-2 appears to be expressed at relatively high levels in early (e.g., 8-day) mouse embryos. The endogenous morphogens may be synthesized by the cells on which they act, by neighboring cells, or by cells of a distant tissue, the secreted protein being transported to the cells to be acted on.

A particularly potent tissue morphogenic protein is OP-1. This protein, and its xenogenic homologs, are expressed in a number of tissues, primarily in tissues of urogenital origin, as well as in bone, mammary and salivary gland tissue, reproductive tissues, and gastrointestinal tract tissue. It is also expressed in different tissues during embryogenesis, its presence coincident with the onset of morphogenesis of that tissue.

The morphogenic protein signal transduction across a cell membrane appears to occur as a result of specific binding interaction with one or more cell surface receptors. Recent studies on cell surface receptor binding of various members of the TGF-β protein superfamily suggests that the ligands can mediate their activity by interaction with two different receptors, referred to as Type I and Type II receptors to form a hetero-complex. A cell surface bound beta-glycan also may enhance the binding interaction. The Type I and Type II receptors are both serine/threonine kinases, and share similar structures: an intracellular domain that consists essentially of the kinase, a short, extended hydrophobic sequence sufficient to span the membrane one time, and an extracellular domain characterized by a high concentration of conserved cysteines.

A number of Type II receptor sequences recently have been identified. These include "TGF-βR II", a TGF-β Type II receptor (Lin et al. (1992) Cell 68: 775–785); and numerous activin-binding receptors. See, for example, Mathews et al. (1991) Cell 65: 973–982 and international patent application WO 92/20793, published Nov. 26, 1992, disclosing the "ActR II" sequence; Attisano et al., (1992) Cell 68: 97–108, disclosing the "ActR-IIB" sequence; and Legerski et al. (1992) Biochem Biophys. Res. Commu. 183: 672–679. A different Type II receptor shown to have affinity for activin is Atr-II (Childs et al.(1993) PNAS 90: 9475–9479.) Two Type II receptors have been identified in C. elegans, the daf-1 gene, (Georgi et al. (1990) Cell 61: 635–645), having no known ligand to date, and daf-4, which has been shown to bind BMP-4, but not activin or TGF-β (Estevez, et al. (1993) Nature 365: 644–649.)

Ten Dijke et al. disclose the cloning of six different Type I cell surface receptors from murine and human cDNA libraries ((1993) Oncogene 8: 2879–2887, and (1994) Science 264: 101–104). These receptors, referenced as ALK-1 to ALK-6 ("activin receptor-like kinases"), share significant sequence identities (60–79%) and several have been identified as TGF-β binding (ALK-5) or activin binding (ALK-2, ALK-4) receptors. Xie et al. also report a Drosophila Type I receptor encoded by the sax gene ((1994) Science 263: 1756–1759). The authors suggest that the protein binds dpp.

To date, a ligand having binding affinity for the ALK-1 Type I receptor has not yet been identified. It is an object of this invention to provide molecules, including OP-1 and OP-1-related proteins, which are competent to act as ligands for ALK-1 receptor binding and/or are capable of mediating an intracellular effect by interaction with the ALK-1 receptor. Another object is to provide methods for identifying genes and naturally occurring sequences in a variety of species and/or tissues, and in a variety of nucleic acid libraries encoding ALK-1 -binding ligands and ALK-1-related receptors. Still another object is to provide means for designing biosynthetic receptor-binding ligand analogs, particularly OP-1 and OP-1-related analogs, and/or for identifying natural-occurring ligand analogs, including agonists and antagonists, using the receptor molecules described herein, and analogs thereof. Another object is to provide antagonists, including soluble receptor constructs comprising the extracellular ligand-binding domain, which can modulate the availability of OP-1 or an OP-1-related protein for ALK-1 receptor binding in vivo. Yet another object is to provide means and compositions for ligand affinity purification and for diagnostic detection and quantification of ligands in a body fluid using an ALK-1 receptor and ligand-binding fragments thereof. Still another object is to provides means and compositions for modulating the endogenous expression or concentration of these receptor molecules. Yet another object is to provide ligand-receptor complexes and analog sequences thereof, as well as antibodies capable of identifying and distinguishing the complex from its component proteins. Still another object is to provide means and compositions for modulating a morphogenesis in a mammal. These and other objects and features of the invention will be apparent from the description, drawings and claims which follow.

SUMMARY OF THE INVENTION

It now has been discovered that the Type I cell surface receptor molecule identified in the literature as ALK-1 is capable of specific binding affinity with true tissue morphogenic proteins, particularly OP-1 and OP-1-related proteins. Accordingly, the invention provides ligand-receptor complexes comprising at least the ligand binding domain of an ALK-1 receptor and OP-1 or an OP-1 related protein or analog thereof as the ligand. The invention also provides means for identifying and/or designing useful receptor sequence analogs and OP-1, OP-1-related proteins, and analogs hereof; and means for modulating the tissue morphogenesis capability of a cell.

The ALK-1 receptor (Seq. ID No. 2) useful in this invention is part of a family of receptor molecules which share a conserved structure, including an extracellular, ligand binding domain generally composed of about 100–130 amino acids (Type I receptors; up to about 196 amino acids for Type II receptors), a transmembrane domain sufficient to span a cellular membrane one time, and an intracellular (cytoplasmic) domain having serine/threonine kinase activity. The intact receptor is a single polypeptide chain of about 500–550 amino acids and having an apparent molecular weight of about 50–55 kDa.

As used herein, ligand-receptor binding specificity is understood to mean a specific, saturable noncovalent interaction between the ligand and the receptor, and which is subject to competitive inhibition by a suitable competitor molecule. Preferred binding affinities (defined as the amount of ligand required to fill one-half (50%) of available receptor binding sites) are described herein by dissociation constant (Kd). In one embodiment, preferred binding affinities of the ligand-receptor complexes described herein have a Kd of less than $10^{-7}$M, preferably less than $5 \times 10^{-7}$M, more preferably less than $10^{-8}$M. In another preferred embodiment, the receptor molecules have little or no substantial binding affinity for TGF-β.

As will be appreciated by those having ordinary skill in the art, the ALK-1 receptor can also have binding affinity for other, related morphogenic proteins. It further is contemplated that one or more related morphogenic proteins may have better binding affinity and/or signal transducing ability than OP-1 has for ALK-1. As used herein, an OP-1-related protein/ALK-1 ligand is understood to have substantially the same binding affinity for ALK-1 as OP-1 if it can be competed successfully for ALK-1 binding in a standard competition assay with OP-1. In one preferred embodiment, the ligand is OP-1 or an OP-1 related protein or analog and has a binding affinity for ALK-1 defined by a dissociation constant of less than about $10^{-7}$M, preferably less than about $5 \times 10^{-7}$M or $10^{-8}$M. It is anticipated however, that analogs having lower binding affinities, e.g., on the order of $10^{-6}$M also will be useful. For example, such analogs may be provided to a mammal to modulate availability of serum-soluble ligand for ALK-1 receptor binding in vivo. Similarly, where tight binding interaction is desired, for example as part of a cancer therapy wherein the analog acts as a ligand-receptor antagonist, preferred binding affinities may be on the order of $5 \times 10^{-8}$M.

In another embodiment, the ALK-1 receptor binding analogs contemplated by the invention include proteins encoded by nucleic acids which hybridize with the DNA sequence encoding OP-1 under stringent hybridization conditions, and which have substantially the same or better binding affinity for a ALK-1 as OP-1. As used herein, stringent hybridization conditions are as defined in the art, (see, for example, *Molecular Cloning: A Laboratory Manual*, Maniatis et al., eds. 2d. ed., Cold Spring Harbor Press, Cold Spring Harbor, 1989.) An exemplary set of conditions is defined as: hybridization in 40% formamide, 5×SSPE, 5×Denhardt's Solution, and 0.1% SDS at 37° C. overnight, and washing in 0.1×SSPE, 0.1% SDS at 50° C.

Useful receptor analogs include xenogenic (foreign species) homologs of the human ALK-1 sequences described herein, including those obtained from other mammalian species, as well as other, eukaryotic, non-mammalian xenogenic homologs. Also contemplated are biosynthetic constructs and naturally-occurring sequence variants of ALK-1, provided these molecules bind OP-1 or an OP-1 related protein, or analog specifically as defined herein. In one embodiment, sequence variants include receptor analogs which have at least the same binding affinity for OP-1 as ALK-1 and which are recognized by an antibody having binding specificity for ALK-1.

The ALK-1 receptor analogs may be used as an OP-1 or an OP-1-related protein antagonist. For example, a soluble form of a receptor, e.g., consisting essentially of only the extracellular ligand binding domain, may be provided systemically to a mammal to bind to soluble ligand, effectively competing with ligand binding to a cell surface receptor, thereby modulating (reducing) the availability of free ligand in vivo for cell surface binding.

The true tissue morphogenic proteins contemplated as useful receptor ligands in the invention include OP-1, OP-1-related proteins, and analogs thereof. As used herein, an "analog" is understood to include all molecules able to functionally substitute for OP-1 or an OP-1-related protein in Type I receptor binding, e.g., which are able to compete successfully with OP-1 for receptor binding in a standard competition assay. In one embodiment, useful analogs include molecules whose binding affinity is defined by a dissociation constant of less than about $5 \times 10M$, preferably less than about $10^{-7}M$ or $5 \times 10^{-7}M$. As described above, both stronger and weaker binding affinities are contemplated to be useful in particular applications.

The OP-1 analogs contemplated herein, all of which mimic the binding activity of OP-1 or an OP-1-related protein sufficiently to act as a substitute for OP-1 in receptor binding, can act as OP-1 agonists, capable of mimicking OP-1 both in receptor binding and in inducing a transmembrane effect e.g., inducing threonine- or serine-specific phosphorylation following binding. Alternatively, the OP-1 analog can act as an OP-1 antagonist, capable of mimicking OP-1 in receptor binding only, but unable to induce a transmembrane effect, thereby blocking the natural ligand from interacting with its receptor, for example. Useful applications for antagonists include their use as therapeutics to modulate uncontrolled differentiated tissue growth, such as occurs in malignant transformations such as in osteosarcomas or Paget's disease.

OP-1 analogs contemplated by the invention can be amino acid-based, e.g., sequence variants of OP-1, or antibody-derived sequences capable of functionally mimicking OP-1 binding to an OP-1-specific receptor. Examples of such antibodies may include anti-idiotypic antibodies. In a specific embodiment, the anti-idiotypic antibody mimics OP-1 both in receptor binding and in ability to induce a transmembrane effect. Alternatively, the OP-1 analogs can be composed in part or in whole of other chemical structures, e.g., the analogs can be comprised in part or in whole of nonproteinaceous molecules. In addition, the OP-1 analogs contemplated can be naturally-sourced or synthetically-produced.

As used herein, an OP-1 related protein contemplates a protein having a sequence sharing at least 60%, preferably greater than 65% or even 70% amino acid sequence homology or "similarity" with the C-terminal 96 amino acid sequence of OP-1 (OPS) as defined in Seq. ID Nos. 3–4, and which is able to substitute for OP-1 in ligand binding to ALK-1, (e.g., able to compete successfully with OP-1 for binding to an ALK-1 receptor.) Proteins sharing at least 60% homology with OP-1 include BMP-2, BMP-4, and GDF-1. In another embodiment an OP-1-related protein is contemplated to include a protein having a sequence sharing at least 60% amino acid sequence homology with the C terminal 102 amino acid sequence of OP-1, (OP-1 "seven cysteine domain.") In one preferred embodiment OP-1 related protein sequences are contemplated to include sequences sharing at least 60%, preferably greater than 65% or even 70% identity with the C-terminal 102 amino acid sequence of OP-1. OP-1 related sequences contemplated by the invention include xenogenic homologs (e.g. the Drosophila homolog 60A), and the related sequences referenced herein and in the literature as OP-2, OP-3, BMP-5, BMP-6 (and its xenogenic homolog Vgr-1.) OP-1 related sequences also include sequence variants encoded by a nucleic acid which hybridizes with a DNA sequence comprising the C-terminal 102 amino acids of Seq. ID No. 3 under stringent hybridization conditions and which can substitute for OP-1 in an OP-1-receptor binding assay. In another embodiment, OP-1 sequence variants include proteins which can substitute for OP-1 in a ligand-receptor binding assay and which is recognized by an antibody having binding specificity for OP-1.

As used herein, "amino acid sequence homology" is understood to mean amino acid sequence similarity, and homologous sequences sharing identical or similar amino acids, where similar amino acids are conserved amino acids as defined by Dayoff et al., *Atlas of Protein Sequence and Structure;* vol. 5, Suppl. 3, pp. 345–362 (M. O. Dayoff, ed., Nat'l BioMed. Research Fdn., Washington D.C. 1978.) Thus, a candidate sequence sharing 60% amino acid homology with a reference sequence requires that, following alignment of the candidate sequence with the reference sequence, 60% of the amino acids in the candidate sequence are identical to the corresponding amino acid in the reference sequence, or constitute a conserved amino acid change thereto. "Amino acid sequence identity" is understood to require identical amino acids between two aligned sequences. Thus, a candidate sequence sharing 60% amino acid identity with a reference sequence requires that, following alignment of the candidate sequence with the reference sequence, 60% of the amino acids in the candidate sequence are identical to the corresponding amino acid in the reference sequence.

As used herein, all OP-1-related protein homologies and identities use OP-1 as the reference sequence, with the C-terminal 102 amino acids described in Seq. ID Nos. 3–4 constituting the seven cysteine domain. Also as used herein, sequences are aligned for homology and identity calculations using the method of Needleman et al. ((1970) *J Mol. Biol.* 48: 443–453), and identities are calculated by the Align program (DNAstar, Inc.). In all cases, internal gaps and amino acid insertions in the candidate sequence as aligned are ignored when making the homology/identity calculation.

In one aspect, the invention contemplates isolated ligand-receptor complexes comprising OP-1 or an OP-1 related protein or analog as the ligand in specific binding interaction with an ALK-1 receptor or receptor analog, as defined herein. In another aspect, the invention contemplates that the ligand-receptor complex also comprises part or all of an OP-1 binding Type II receptor. Type II receptors contemplated to be useful include Type II receptors defined in the literature as having binding specificity for activin or a bone morphogenic protein, including daf-4, ActRII and AtrII. In still another aspect, the ligand-receptor complex comprises both a Type I and a Type II receptor and OP-1, or an OP-1 related protein or analog as the ligand. In all complexes, the bound receptor may comprise just the extracellular, ligand binding domain, or may also include part or all of the transmembrane sequence, and/or the intracellular kinase domain. Similarly, the ligand may comprise just the receptor binding sequence, longer sequences, including the mature dimeric species or any soluble form of the protein or protein analog.

In another aspect, the invention contemplates binding partners having specific binding affinity for an epitope on the ligand-receptor complex. In a preferred embodiment, the binding partner can discriminate between the complex and the uncomplexed ligand or receptor. In another embodiment, the binding partner has little or no substantial binding affinity for the uncomplexed ligand or receptor. In another preferred embodiment, the binding partner is a binding protein, more preferably an antibody. These antibodies may be monoclonal or polyclonal, may be intact molecules or fragments thereof (e.g., Fab, Fab', (Fab)'$_2$), or may be biosynthetic derivatives, including, but not limited to, for example, monoclonal fragments, such as single chain $F_v$ fragments, referred to in the literature as s$F_v$s, BABs and SCAs, and chimeric monoclonals, in which portions of the monoclonals are humanized (excluding those portions involved in antigen recognition (e.g., complementarity determining regions, "CDRs".) See, for example, U.S. Pat. Nos. 5,091,513 and 5,132,405, the disclosures of which are incorporated herein by reference. Biosynthetic chimeras, fragments and other antibody derivatives may be synthesized using standard recombinant DNA methodology and/or automated chemical nucleic acid synthesis methodology well described in the art and as described below.

In still another aspect, the invention provides molecules useful in the design and/or identification of morphogenic protein analogs as described below, as well as kits and methods, e.g., screening assays, for identifying these analogs. The molecules useful in these assays can include part or all of the ALK-1 receptor sequence of Seq. ID No. 2, including analogs and amino acid sequence variants thereof. Currently preferred for these assays are receptor sequences comprising at least the sequence which defines the extracellular, ligand binding domains. Similarly, the kits and screening assays can be used in the design and/or identification of ALK-1 receptor analogs. The OP-1 analogs and OP-1 receptor analogs identified then can be produced in reasonable quantities using standard recombinant expression or chemical synthesis technology.

In still another aspect, the receptor and/or OP-1-specific receptor analogs can be used in standard methodologies for affinity purifying and/or quantifying OP-1, OP-1-related proteins and analogs. For example, the receptor's ligand binding domain first may be immobilized on a surface of a well or a chromatographic column; ligand in a sample fluid then may be provided to the receptor under conditions to allow specific binding; non-specific binding molecules then removed, e.g., by washing, and the bound ligand then selectively isolated and/or quantitated. Similarly, OP-1, OP-1-related proteins and OP-1 analogs can be used for affinity purifying and/or quantifying ALK-1 receptors and receptor analogs. In one embodiment, the method is useful in kits and assays for diagnostic purposes which detect the presence and/or concentration of OP-1 protein or related morphogen in a body fluid sample including, without limitation, serum, peritoneal fluid, spinal fluid, and breast exudate. The kits and assays can also be used for detecting and/or quantitating ALK-1 receptors in a sample.

In still another aspect the invention comprises ALK-1 receptors and receptor analogs useful in screening assays to identify organs, tissues and cell lines which express ALK-1 receptors. These cells then can be used in screening assays to identify ligands that modulate endogenous morphogen receptor expression levels, including the density of receptors expressed on a cell surface. Useful assay methodologies may be modeled on those described in PCT US92/07359, and as described below.

The invention thus relates to compositions and methods for the use of morphogen receptor sequences in diagnostic, therapeutic and experimental procedures. Active receptors useful in the compositions and methods of this invention can include truncated or full length forms, as well as forms having varying glycosylation patterns. Active receptors useful in the invention also include chimeric constructs as described below. Active OP-1-specific receptors/analogs can be expressed from intact or truncated genomic or cDNA, or from synthetic DNAs in prokaryotic or eukaryotic host cells, and purified, cleaved, refolded and oxidized as necessary to form active molecules. Useful host cells include prokaryotes, including $E.$ $coli$ and $B.$ $subtilis,$ and eukaryotic cells, including mammalian cells, such as fibroblast 3T3 cells, CHO, COS, melanoma or BSC cells, Hela and other human cells, the insect/baculovirus system, as well as yeast and other microbial host cell systems.

Thus, in view of this disclosure, skilled genetic engineers now can, for example, identify and produce ALK-1 cell surface receptors or analogs thereof; create and perform assays for screening candidate OP-1 or OP-1-related protein analogs and evaluate promising candidates in therapeutic regimes and preclinical studies; modulate the availability of endogenous morphogen for cell surface interactions; modulate endogenous ALK-1 cell surface receptor levels; elucidate the signal transduction pathway induced or otherwise mediated by ALK-1 receptor binding; and modulate tissue morphogenesis in vivo.

BRIEF DESCRIPTION OF THE DRAWINGS

FIG. 1 is a schematic representation of OP-1-induced PAI-1 production in cells transfected with ALK-1, ALK-3 or ALK-5;

DETAILED DESCRIPTION

Figure 2A:
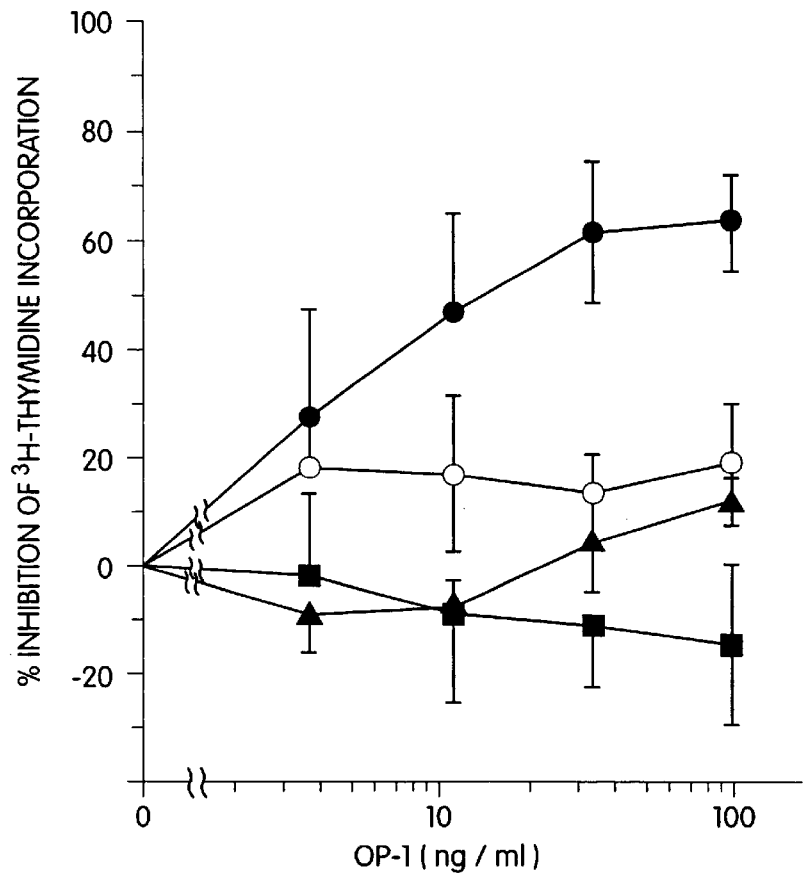
FIG. 2A is a graphic representation of $^3$H-thymidine incorporation in response to OP-1 in R4-2 cells transfected with ALK-1 (closed circles), ALK-3 (closed triangles) and ALK-5 (closed squares) as a function of OP-1 concentration.

Disclosed herein is a Type I receptor, ALK-1, having binding specificity for true tissue morphogenic proteins, particularly OP-1 and OP-1-related proteins. The ALK-1 Type I receptors disclosed herein, can be used together with OP-1, OP-1-related proteins and OP-1 analogs for therapeutic, diagnostic and experimental uses as described herein below. Moreover, soluble forms of the receptor proteins, e.g., forms consisting essentially of the extracellular domain or a fragment thereof sufficient to bind OP-1 with specificity, can be used as a soluble therapeutic morphogen antagonist, as described below.

Following this disclosure, related ALK-1 receptors are available, as are high and medium flux screening assays for identifying ligand analogs and ALK-1 receptor analogs. These analogs can be naturally occurring molecules, or they can be designed and biosynthetically created using a rational drug design and an established structure/function analysis. The analogs can be amino acid-based or can be composed in part or whole of non-proteinaceous synthetic organic molecules. Useful analogs also can include antibodies, preferably monoclonal antibodies (including fragments thereof, e.g., Fab, Fab', and (Fab)'$_2$), or synthetic derivatives thereof, such as monoclonal single chain F$_v$ fragments known in the art as sF$_v$s, BABs, and SCAs (see below), and bispecific antibodies or derivatives thereof. When these antibodies mimic the binding activity of OP-1 to a cell surface receptor without inducing the biological response OP-1 does upon binding, the antibody can compete for OP-1 binding and act as an antagonist. These antibodies or derivatives thereof can also mimic OP-1 both in receptor binding and signal transduction, in which case the antibody acts as an OP-1 agonist. The antibodies and derivatives can also be used for inducing the morphogenic cellular response by crosslinking receptors to morphogenic proteins, particularly OP-1 and OP-1-related proteins to form either homo- or heterocomplexes of the Type I and Type II receptors.

The ALK-1 receptor sequences described herein also can be used to create chimeric sequences, wherein, for example, part or all of either the extracellular domain or the intracellular domain is a non-ALK sequence or is created from two or more ALK sequences. These chimeric receptors can be synthesized using standard recombinant DNA methodology and/or automated chemical nucleic acid synthesis methodology well described in the art and as disclosed below. Chimerics can be used, for example, in OP-1 analog assays, wherein the OP-1-binding extracellular domain is coupled to a non-ALK intracellular domain that is well characterized and/or readily detectable as a second messenger response system, as described below. Chimerics can also be used, for example, in high flux OP-1 analogs screens and as part of purification protocols, wherein a soluble ligand binding domain of an OP-1-specific receptor is immobilized on to a support e.g., by covalent or non-covalent interactions, with a chromatographic matrix or the well surface of a 96-well plate. When immobilized onto a chromatographic matrix surface, the receptor fragment can be used in a protocol to isolate OP-1 or OP-1 analogs. When immobilized on a well surface the receptor fragment is particularly useful in a screening assay to identify receptor-binding OP-1 analogs in a standard competition assay.

The true tissue morphogenic proteins contemplated to be useful in the methods and compositions of the invention include forms having varying glycosylation patterns and varying N-termini. The proteins can be naturally occurring or biosynthetically derived, and can be produced by expression of recombinant DNA in prokaryotic or eukaryotic host cells. The proteins are active as a single species (e.g., as homodimers), or combined as a mixed species. Useful sequences and eukaryotic and prokaryotic expression systems are well described in the art. See, for example, U.S. Pat. Nos. 5,061,911 and 5,266,683 for useful expression systems.

Contemplated herein are OP-1 and OP-1-related sequences. Particularly useful OP-1 sequences are recited in U.S. Pat. Nos. 5,011,691; 5,018,753 and 5,266,683; in Ozkaynak et al. (1990) *EMBO J* 9: 2085–2093; and Sampath et al. (1993) *PNAS* 90: 6004–6008. OP-1 related sequences include xenogenic homologs, e.g.; 60A, from Drosophila, Wharton et al. (1991) *PNAS* 88: 9214–9218; and proteins sharing at least 60% amino acid sequence homology or "similarity" with OP-1 in the C-terminal seven cysteine domain. In a preferred embodiment, the related proteins share greater than 60% identity in the C-terminal seven cysteine domain, preferably at least 65% identity. Examples of OP-1 related sequences include BMP-5, BMP-6 (and its species homolog Vgr-1, Lyons et al. (1989) *PNAS* 86: 4554–4558), Celeste, et al. (1990) *PNAS* 87: 9843–9847 and PCT international application WO 93/00432; OP-2 (Ozkaynak et al. (1992) *J Biol. Chem.* 267: 13198–13205) and OP-3 (PCT international application WO 94/06447). As will be appreciated by those having ordinary skill in the art, chimeric constructs readily can be created using standard molecular biology and mutagenesis techniques combining various portions of different morphogenic protein sequences to create a novel sequence, and these forms of the protein also are contemplated herein.

A particularly preferred embodiment of the proteins contemplated by the invention includes proteins whose amino acid sequence in the cysteine-rich C-terminal domain has greater than 60% identity, and preferably greater than 65% identity with the amino acid sequence of OPS (OP-1 sequence defining the C-terminal conserved six cysteines, e.g., residues 335–431 of Seq. ID Nos. 3–4).

In another preferred aspect, the invention contemplates osteogenic proteins comprising species of polypeptide chains having the generic amino acid sequence herein referred to as "OPX" which accommodates the homologies between the various identified species of the osteogenic OP-1 and OP-2 proteins, and which is described by the amino acid sequence presented below and in Seq. ID No. 5.

```
Cys Xaa Xaa His Glu Leu Tyr Val Ser Phe
 1               5                   10
Xaa Asp Leu Gly Trp Xaa Asp Trp Xaa Ile
                15                   20
Ala Pro Xaa Gly Tyr Xaa Ala Tyr Tyr Cys
                25                   30
Glu Gly Glu Cys Xaa Phe Pro Leu Xaa Ser
                35                   40
Xaa Met Asn Ala Thr Asn His Ala Ile Xaa
                45                   50
Gln Xaa Leu Val His Xaa Xaa Xaa Pro Xaa
                55                   60
Xaa Val Pro Lys Xaa Cys Cys Ala Pro Thr
                65                   70
Xaa Leu Xaa Ala Xaa Ser Val Leu Tyr Xaa
                75                   80
Asp Xaa Ser Xaa Asn Val Ile Leu Xaa Lys
                85                   90
Xaa Arg Asn Met Val Val Xaa Ala Cys Gly
                95                  100
Cys His,
``` and wherein Xaa at res. 2=(Lys or Arg); Xaa at res. 3=(Lys or Arg); Xaa at res. 11=(Arg or Gln); Xaa at res. 16=(Gln or Leu); Xaa at res. 19=(Ile or Val); Xaa at res. 23=(Glu or Gln); Xaa at res. 26=(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn); Xaa at res. 61=(Thr, Ala or Val); Xaa at res. 65=(Pro or Ala); Xaa at res. 71 =(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Ser or Asn); Xaa at res. 89=(Lys or Arg); Xaa at res. 91=(Tyr or His); and Xaa at res. 97=(Arg or Lys).

In still another preferred aspect, the invention contemplates osteogenic proteins encoded by nucleic acids which hybridize to DNA or RNA sequences encoding the C-terminal seven cysteine domain of OP-1 or OP-2 under stringent hybridization conditions.

A brief description of the various terms of OP-1 useful in the invention is described below:

OP-1—Refers generically to the family of osteogenically active proteins produced by expression of part or all of the hOP-1 gene. Also referred to in related applications as "OPI" and "OP-1".

OP-1-PP—Amino acid sequence of human OP-1 protein (prepro form), Seq. ID Nos. 3–4, residues 1–431. Also referred to in related applications as "OP-1-PP" and "OPP".

OP-1-18Ser—Amino acid sequence of mature human OP-1 protein, Seq. ID Nos. 3–4, residues 293–431. N-terminal amino acid is serine. Originally identified as migrating at 18 kDa on SDS-PAGE in COS cells. Depending on protein glycosylation pattern in different host cells, also migrates at 23 kDa, 19 kDa and 17 kDa on SDS-PAGE. Also referred to in related applications as "OP-1-1-8."

OP-1–16Ser; OP-1–16Ala; OP-1–16Met; OP-1–16Leu; OP-1–16Val—N-terminally truncated mature human OP-1 protein species defined, respectively, by residues 300–431; 316–431; 315–431; 313–431 and 318–431 of Seq. ID Nos. 3–4.

OPS—Amino acid sequence defining the C-terminal six cysteine domain, residues 335–431 of Seq. ID Nos. 3–4.

OP7—Amino acid sequence defining the C-terminal seven cysteine domain, residues 330–431 of Seq. ID Nos. 3–4.

Soluble form OP-1—mature dimeric OP-1 species having one or, preferably two copies of pro domain, e.g., at least residues 158–292 of Seq. ID Nos. 3–4, preferably residues 48–292 or 30–292, non-covalently complexed with the dimer.

The cloning procedure for obtaining OP-1-binding ALK nucleic acid sequences, means for expressing receptor sequences, as well as other material aspects concerning the nature and utility of these sequences, including how to make and how to use the subject matter claimed, will be further understood from the following, which constitutes the best mode currently contemplated for practicing the invention.

EXAMPLE 1

Identification of ALK-1

The cloning and characterization of ALK-1, -2, -3, and -6 receptors are described in detail in ten Dijke et al. (1993) *Oncogene* 8: 2879–2887; and (1994) *Science* 264: 101–104. These molecules have similar domain structures: an N-terminal predicted hydrophobic signal sequence (von Heijne (1986) *Nucl. Acids Res.* 14: 4683–4690) is followed by a relatively small extracellular cysteine-rich ligand binding domain, a single hydrophobic transmembrane region (Kyte & Doolittle (1982) *J Mol. Biol.* 157: 105–132) and a C-terminal intracellular portion, which consists almost entirely of a kinase domain.

The extracellular domains of the ALK-1 receptor is defined essentially by residues 22–118 (Seq. ID Nos. 1–2).

The positions of many of the cysteine residues in these receptors can be aligned, indicating that the extracellular domains likely adopt a similar structural configuration.

The intracellular domains of these receptors are characterized by a serine/threonine kinase, defined essentially by residues 204–494 (Seq. ID Nos. 1–2) for ALK-1. The catalytic domains of kinases can be divided into 12 subdomains with stretches of conserved amino-acid residues. The key motifs are found in serine/threonine kinase receptors indicating that they are functional kinases. The consensus sequence for the binding of ATP (Gly—X—Gly—X—X—Gly (SEQ ID NO: 6) in subdomain I followed by a Lys residue further downstream in subdomain II) is found in all the ALK. Moreover, ALK-1, ALK-2, ALK-3 and ALK-6 have the sequence motifs or similar motifs HRDLKSKN (SEQ ID NO: 7) (Subdomain VIB) and GTKRYMAPE (SEQ ID NO: 8) (Subdomain VIII), that are found in most of the serine/threonine kinase receptors and can be used to distinguish them from tyrosine kinase receptors. Two short inserts in the kinase domain (between subdomain VIA and VIB and between X and XI are unique to members of this serine/threonine kinase receptor family. In the intracellular domain, these regions, together with the juxtamembrane part and C-terminal tail, are the most divergent between family members.

EXAMPLE 2

Receptor Expression

A. General Considerations

Receptor DNA, or a synthetic form thereof, can be inserted, using conventional techniques well described in the art (see, for example, Maniatis (1989) *Molecular Cloning A Laboratory Manual*), into any of a variety of expression vectors and transfected into an appropriate host cell to produce recombinant protein polypeptide chains, including both full length and truncated forms thereof. Shortened sequences, for example, can be used for the production of soluble receptor fragments.

Useful host cells include *E. coli, Saccharomyces cerevisiae, Pichia pastoris*, the insect/baculovirus cell system, myeloma cells, and various other mammalian cells. The full length forms of the proteins of this invention preferably are expressed in mammalian cells, as disclosed herein. Soluble forms may be expressed from both mammalian or bacterial cell systems. The vector additionally may include various sequences to promote correct expression of the recombinant protein, including transcription promoter and termination sequences, enhancer sequences, preferred ribosome binding site sequences, preferred MRNA leader sequences, preferred protein processing sequences, preferred signal sequences for protein secretion, and the like. The DNA sequence encoding the gene of interest also may be manipulated to remove potentially inhibiting sequences or to minimize unwanted secondary structure formation. The recombinant morphogen receptor also may be expressed as a fusion protein. After translation, the protein may be purified from the cells themselves or recovered from the culture medium. The DNA also may include sequences which aid in expression and/or purification of the recombinant protein. One useful sequence for example, is a hexa-His ($His_6$) sequence, which adds a histidine tail to allow affinity purification of the protein on an $Cu^{2+}$ IMAC column (see below.)

For example, the DNA encoding the extracellular domain may be inserted into a suitable expression vector for transformation into a prokaryote host such as *E. coli* or *B. subtilis*, to produce a soluble, morphogen binding fragment. The DNA may expressed directly or may be expressed as part of a fusion protein having a readily cleavable fusion junction. An exemplary protocol for prokaryote expression using MR-1 DNA is provided below. Recombinant protein is expressed in inclusion bodies and may be purified therefrom using the technology disclosed in U.S. Pat. No. 5,013,653, for example.

The DNA also may be expressed in a suitable mammalian host. Useful hosts include fibroblast 3T3 cells, (e.g., NIH 3T3, from CRL 1658) COS (simian kidney ATCC, CRL-1650) or CHO (Chinese hamster ovary) cells (e.g., CHO-DXB11, from Lawrence Chasin, (1980) *PNAS* 77: 4216–4222), mink-lung epithelial cells (MV1Lu), human foreskin fibroblast cells, human glioblastoma cells, and teratocarcinoma cells. Other useful eukaryotic cell systems include yeast cells, the insect/baculovirus system or myeloma cells.

To express an ALK-1 cell surface receptor, the DNA is subcloned into an insertion site of a suitable, commercially available vector along with suitable promoter/enhancer sequences and 3' termination sequences. Useful promoter/enhancer sequence combinations include the CMV promoter (human cytomegalovirus (NHE) promoter) present, for example, on pCDM8, as well as the mammary tumor virus promoter (MMTV) boosted by the Rous sarcoma virus LTR enhancer sequence (e.g., from Clontech, Inc., Palo Alto). Expression also may be further enhanced using transactivating enhancer sequences. The plasmid also preferably contains an amplifiable marker, such as DHFR under suitable promoter control, e.g., SV40 early promoter (ATCC #37148). Transfection, cell culturing, gene amplification and protein expression conditions are standard conditions, well known in the art, such as are described, for example in Ausubel et al., ed., *Current Protocols in Molecular Biology*, John Wiley & Sons, N.Y. (1989). Briefly, transfected cells are cultured in medium containing 5–10% dialyzed fetal calf serum (FCS), and stably transfected high expression cell lines obtained by amplification and subcloning and evaluated by standard Western and Northern blot analysis. Southern blots also can be used to assess the state of integrated receptor sequences and the extent of their copy number amplification.

The expressed protein then is purified using standard procedures. A currently preferred methodology uses an affinity column, such as a ligand affinity column or an antibody affinity column, the bound material then washed, and receptor molecules selectively eluted in a gradient of increasing ionic strength, changes in pH or addition of mild denaturants. Alternatively, where a useful anchor sequence has been added to the DNA, such as a $(His)_6$ sequence, the column may be a standard affinity column such as $Cu^{2+}$ IMAC column. Here, for example, the cell culture media containing the recombinant protein is passed over a $Cu^{2+}$ IMAC column (for example, prepared with 25 mM imidazole). The bound protein then is washed with a compatible solution and eluted with EDTA. The anchor sequence can be removed by a standard chemical or enzymatic procedure.

Mammalian cell expression is preferred where morphogen receptor expression on a cell surface is desired. For example, cell surface expression may be desired to test morphogen or morphogen analog binding specificity for a cell surface receptor under in vivo conditions. Cell surface expression also may be most efficacious for medium flux cellular screen assays as described below.

B.1 Exemplary Mammalian Cell Culture

The receptors described herein and tested in Example 8 described below, were expressed in (1) COS-1 cells; (2) mink lung epithelial cells (Mv1Lu); and (3) ATDC5, a chondrogenic cell line, (Atnami (1990) *Cell Diff Dev.* 30: 109–116). They also can be tested in a variety of other cells including, without limitation, AG1518 human foreskin fibroblasts; MG-63 human osteosarcoma cells; PC12 rat pheochromocytoma cells (all obtainable from American Type Culture Collection, Rockville, Md.); human glioblastoma cells (U-1240MG, Bengt Westermark, et al. (1988) *Cancer Research* 48: 3910$^{-3918}$); Tera-2 teratocarcinoma cells (clone 13, Thompson et al. (1984) *J Cell Sci* 72: 37–64); MC3T3-E1 cells (Sudo et al. (1983) *J Cell Biol.* 96: 191–198, and ROS 17/2.8 rat osteosarcoma cells (Majeska et al. (1985) *Endocrinology* 116: 170–179. Exemplary culturly conditions for the ROS cells include culture in Ham's F12 medium containing 14 mM HEPES buffer, 2.5 mM L-glutamine, 1.1 mM $CaCl_2$, 5% fetal bovine serum and antibiotics; for MC3T3-E1 cells, culture in a-MEM with 10% fetal bovine serum and antibiotics, and for Tera-2 cells culture in 5% $CO_2$ atmosphere at 37° C. in a-MEM containing 10% fetal bovine serum, 100 units/ml of penicillin and 50 mg/ml of streptomycin, using tissue culture dishes pretreated with 0.1% swine skin gelatin (Sigma) in phosphate-buffered saline. Unless otherwise specified, in the examples provided herein, cells were cultured in DMEM containing 10% fetal bovine serum and antibiotics.

EXAMPLE 3

Antibody Production

A. General Considerations

Antibodies capable of specifically binding the receptor molecules, ligand molecules, or the ligand-receptor complex itself, useful as analogs and useful in immunoassays and in the immunopurification of morphogen receptors described may be obtained as described below.

Where antibodies specific to the ALK-1 receptors are desired, but which do not interfere with ligand binding, the antigenic sequence preferably comprises the juxtamembrane sequence. Where antibodies capable of competing for ligand binding are desired, the ligand binding domain may be used as the antigen source. Where antibodies to the complex are desired, the complex itself preferably is used as the antigenic sequence and candidate antibodies then tested for cross reactivity with uncomplexed ligand and receptors versus the ligand-receptor complex. Finally, bispecific antibodies may used to complex ligand to a cell surface receptor (Type I or Type II) and/or to target an agent or ligand to cells or tissue expressing a Type I or Type II morphogen-specific receptor. Preferred bispecific antibody derived molecules are single chain binding sites described in U.S. Pat. No. 5,091,513 and 5,132,405, the disclosures of which are incorporated hereinabove by reference.

Antibodies useful as OP-1 analogs may be obtained using the receptor ligand binding domain as the immunogen source and testing receptor-binding analogs for their ability to compete with OP-1 in a competition binding assay. Similarly, where antibodies useful as OP-1-specific receptor analogs are desired, OP-1 is the immunogen source and the antibody tested in a competition assay with receptor protein.

Polyclonal antibodies specific for a morphogen receptor of interest may be prepared generally as described below. Each rabbit is given a primary immunization (e.g., 500 mg) of antigen in 0.1% SDS mixed with 500 ml Complete Freund's Adjuvant. The antigen is injected intradermally at multiple sites on the back and flanks of the animal. The rabbit is boosted after a month with 500 mg of antigen in the same manner using incomplete Freund's Adjuvant. Test bleeds are taken from the ear vein seven days later. Two additional boosts and test bleeds are performed at monthly intervals until antibody against the antigenic sequence is detected in the serum using a standard Western blot. Then, the rabbit is boosted monthly with 100 mg/ml of antigen and bled (15 ml per bleed) at days seven and ten after boosting.

Similarly, monoclonal antibodies specific for a given morphogen receptor molecule of interest may be prepared as described below: A mouse is given two injections of the antigenic sequence. The protein preferably is recombinantly produced. Where it is desired that the antibody recognize an epitope on the morphogen binding surface of a receptor an antigenic fragment derived from the extracellular domain preferably is provided. The first injection contains 100 mg of antigen in complete Freund's adjuvant and is given subcutaneously. The second injection contains 50 mg of antigen in incomplete adjuvant and is given intraperitoneally. The mouse then receives a total of 230 mg of antigen in four intraperitoneal injections at various times over an eight month period. One week prior to fusion, the mouse is boosted intraperitoneally with antigen (e.g., 100 mg) and may be additionally boosted with an antigen-specific peptide conjugated to bovine serum albumin with a suitable crosslinking agent. This boost can be repeated five days (IP), four days (IP), three days (IP) and one day (IV) prior to fusion. The mouse spleen cells then are fused to commercially available myeloma cells at a ratio of 1:1 using PEG 1500 (Boehringer Mannheim, Germany), and the fused cells plated and screened for ALK-specific antibodies using ALK-1, ALK-2, ALK-3 or ALK-6 as antigen. The cell fusion and monoclonal screening steps readily are performed according to standard procedures well described in standard texts widely available in the art. (See, for example, *Guide to Protein Purification* Murray P. Deutscher, ed., Academic Press, San Diego, 1990.

B. Exemplary ALK-Specific Antisera

Antibodies used in the assays described herein were obtained as reported in Franzen et al. (1993) *Cell* 75: 885–892, and ten Dijla et al. (1994) *Science* 264: 101–104. Briefly, rabbit antisera against ALK-1 were made against synthetic peptides corresponding to the divergent, intracellular juxtamembrane parts: residues 119–141. Peptides were synthesized with an Applied Biosystems 430 A Peptide Synthesizer using t-butoxycarbonyl chemistry, and purified by reverse phase HPLC. The synthetic peptides were coupled to keyhole limpet hemocyanin (Calbiochem-Behring) using glutaraldehyde, as described by Gullick et al. (1985) *EMBO J* 4: 2869–2877. The coupled peptides then were mixed with Freund's adjuvant and used to immunize rabbits using standard methodologies.

EXAMPLE 4

OP-1-Receptor Binding Assays

Ligand binding specificity is determined by evaluating the ability of a receptor molecule to bind a specific ligand, and the ability of that ligand to compete against itself and other molecules which bind the receptor. Useful ligands will have a binding affinity for a soluble morphogen receptor extracellular domain such that dissociation constant (Kd) is less than about $10^{-6}$M, preferably less than $5\times10^{-7}$M. Where stronger binding interaction is desired, preferred affinities are defined by a Kd of $10^{-8}$–$10^{-9}$M. OP-1-related proteins are expected to be able to bind with specificity to multiple different receptor molecules, although likely with differing affinities.

Ligand binding specificity can be assayed as follows, essentially following standard protocols well described in the art and disclosed, for example, in Legerski et al. (1992) *Biochem. Biophys. Res. Comm.* 183: 672–679 and Frakar et al., (1978) *Biochem. Biophys. Res. Comm.* 80: 849–857. In the ligand binding assays, a ligand having a known, quantifiable affinity for a morphogen receptor molecule of interest is labeled, typically by radioiodination ($^{125}$I), e.g., by chromogenic or fluorogenic labeling, or by metabolic labeling, e.g., $^{35}$S, and aliquots of cells expressing the receptor on their surface are incubated with the labeled ligand, in the presence of various concentrations of unlabeled potential competitor ligand. In the assays described in Examples 8 and 9, below, this competitor typically is the candidate morphogen analog or an aliquot from a broth or extract anticipated to contain a candidate morphogen analog.

Alternatively, a crosslinking agent may be used to covalently link the ligand to the bound receptor, and the crosslinked complex then immunoprecipitated with an antibody specific to the ligand, receptor, or complex.

A standard, exemplary protocol for determining binding affinity is provided below. Briefly, cells expressing a receptor on their cell surface are plated into 35 mM dishes and incubated for 48 hours in DMEM (Dulbecco's modified Eagle medium) plus 10% fetal calf serum. Purified morphogen, here, e.g., OP-1, or an OP-1-analog is iodinated with Na$^{125}$I by chloramine T oxidation, preferably having a specific activity of about 50–100 mCi/mg, essentially following the protocol of Frolik et al. (1984) *J Biol. Chem.* 595: 10995–11000. Labeled morphogen then is purified using standard procedures, e.g., chromatographically. Plated cells then are washed twice with physiologically buffered saline in the presence of 0.1% BSA, and incubated at 22° C. in the presence of BSA, buffer and labeled morphogen (1 ng) and various concentrations (e.g., 0–10 mg/ml) of unlabeled competitor, e.g., unlabeled morphogen or candidate ligand analogs. Following binding, cells are washed three times with cold buffer, solubilized in 0.5 ml of 0.5N NaOH, removed from the dish, and radioactivity determined by gamma or scintillation counter. Data then are expressed as percent inhibition, where 100% inhibition of specific binding is the difference between binding in the absence of competitor and binding in the presence of a 100-fold molar excess of unlabeled morphogen. Binding parameters preferably are determined using a computer program such as LIGAND (Munsun et al. (1980) *Anal. Biochem.* 107: 220–259.)

Where the receptor cell surface binding domain is to be provided as a soluble protein, the assay can be performed in solution, most readily as an immunoprecipitation assay. In currently preferred assays the morphogen molecule is labeled and incubated with unlabeled receptor and candidate morphogen analogs. Receptor-specific antibody then is provided to the solution to precipitate the receptor-morphogen complex and the amount of labeled morphogen in the precipitated complex determined using standard detection means.

Where the receptor or ligand is to be used in an affinity isolation protocol, the molecule preferably is immobilized on a surface, preferably a matrix surface over which sample fluid will flow, allowing the ligand of interest to bind, at letting nonbinding components pass through as effluent. The complex then can be removed intact or the ligand selectively removed with a desired eluant.

4.1 Screening Assay Considerations

In an analog screening assay, the currently preferred protocol is a standard competition or radioimmunoassay (RIA). Here the OP-1 is labeled and the relative binding affinity of a candidate OP-1 analog ligand in a sample is measured by quantitating the ability of the candidate (unlabeled ligand analog) to inhibit binding of the labeled ligand (competitor morphogen) by the receptor. In performing the assay, fixed concentrations of receptor and labeled morphogen are incubated in the absence and presence of unknown samples containing candidate ligands. Sensitivity can be increased by preincubating the receptor with candidate ligand before adding the labeled morphogen. After the labeled competitor has been added, sufficient time is allowed for adequate competitor binding, and then free and bound labeled morphogen are separated, and one or the other is measured. Useful morphogen labels include radioactive labels, chromogenic or fluorogenic labels, and conjugated enzymes having high turnover numbers, such as horseradish peroxidase, alkaline phosphatase, or b-galactosidase, used in combination with chemiluminescent or fluorogenic substrates. In the same manner, OP-1-specific receptor analogs can be assayed for their affinity for OP-1 in competition assays with labeled OP-1 specific receptors.

4.2 Diagnostic Assay Considerations

The ability to detect morphogens in solution provides a valuable tool for diagnostic assays, allowing one to monitor the level of morphogen free in the body, e.g., in serum, urine, spinal or peritoneal fluid, breast exudate, and other body fluids.

For example, OP-1 is an intimate participant in normal bone growth and resorption. Thus, soluble OP-1 is expected to be detected at higher concentrations in individuals experiencing high bone formation, such as children, and at substantially lower levels in individuals with abnormally low rates of bone formation, such as patients with osteoporosis, aplastic bone disease, or osteopenia. Monitoring the level of OP-1 in serum thus provides a means for evaluating the status of bone tissue and bone homeostasis in an individual, as well as a means for monitoring the efficacy of a treatment to regenerate damaged or lost bone tissue.

For serum assays, the serum preferably first is partially purified to remove some of the excess, contaminating serum proteins, such as serum albumin. Preferably the serum is extracted by precipitation in ammonium sulfate (e.g., 45%) such that the complex is precipitated. Further purification can be achieved using purification strategies that take advantage of the differential solubility of soluble morphogen complex or mature morphogens relative to that of the other proteins present in serum. Further purification also can be achieved by chromatographic techniques well known in the art. The sample fluid then can be assayed for OP-1 using the OP-1-specific receptor(s) and binding assays as described herein.

Morphogens useful in the binding/screening assays contemplated herein include the soluble forms of the protein, e.g., the mature dimeric species complexed with one or two copies of the pro domain, the mature dimeric species alone, and truncated forms comprising essentially just the C-terminal active domain.

EXAMPLE 5

Transmembrane Signal Induction Assays/OP-1Mimetics

The kinase activity of the intracellular domains of the ALK-1 receptors can be tested in an autophophorylation assay as described by Mathews et al. (PCT/US92/03825, published Nov. 26, 1992). Briefly, the DNA fragment encoding at least the intracellular kinase domain of an OP-1-specific receptor is subcloned into pGEX-2T (Smith et al. (1988) Gene 67: 31–40) to create a fusion protein between the putative kinase domain and glutathione S-transferase (GST). The plasmid is introduced into E. coli and the expressed fusion protein purified using glutathione affinity chromatography. About 100–200 ng of fusion protein or purified GST then are incubated with 25 mCi (gp$^{32}$p) ATP in 50 mM Tris, 10 mM MgCl$_2$ buffer for 30 minutes at 37° C. Products then are analyzed by gel electrophoresis and autoradiography. The fusion protein, but not GST alone, becomes phosphorylated, indicating that the kinase domain is functional. Phosphoamino acid analysis then can be performed to determine the predominant amino acid being phosphorylated. Similar assays can be performed using similar fusion constructs expressed in mammalian cells.

Various signaling transduction assays are provided in Example 9, below. An assay can also be developed for testing kinase activity transduction upon ligand binding using a ligand-induced kinase activity assay known in the art. Here, the ability of OP-1 analog to induce phosphorylation upon binding to the receptor is tested.

See, for example, various assays for measuring ligand-induced kinase activity described by Accili et al. (1991) J Biol. Chem. 266: 434–439 and Nakamura et al. (1992) J Biol. Chem. 267: 18924–18928. For example, ligand-induced kinase activity (e.g., receptor autophosphorylation) can be measured in vitro by incubating purified receptor in the presence and absence of ligand (here, OP-1 or OP-1 analog, e.g., $10^{-7}$M) under conditions sufficient to allow binding of the ligand to the receptor, followed by exposure to $^{32}$P-ATP (e.g., 100 mCi in the presence of 10 mM Tris-HCl (pH 7.6), 10 mM MgCl$_2$, 10 mM MnCl$_2$, 1 mM dithiothreitol, 0.15M NaCl, 0.1% Triton X-100 and 3% glycerol) and the amount of phosphorylation measured, e.g., by SDS polyacrylamide gel electrophoresis and autoradiography following immunoprecipitation with antiphosphoserine, antiphosphothreonine or antiphosphotyrosine antibody (e.g., commercially available or made using standard antibody methodologies.) While a low level of autophosphorylation may be detected in the absence of ligand, incubation with ligand is anticipated to significantly increase (e.g., 5–20 fold increase) the amount of phosphorylation detected.

In another assay for detecting ligand-induced receptor autophosphorylation, involving intact cells, receptor DNA is transfected into a suitable host cell, e.g., a fibroblast, which then is grown under standard conditions to create a confluent monolayer of cells expressing the receptor on their cell surface. On the day of the experiment, cells are incubated with or without ligand (e.g., OP-1 or OP-1 analog, e.g., $10^{-7}$M) at 37° C., and then quickly washed with a "stopping solution" containing ATP (e.g., 0.1M NaF, 4 mM EDTA, 10 mM ATP, 10 mM sodium orthovanadate, 4 mM sodium pyrophosphate). The cells then are frozen in a dry ice/ ethanol bath, solubilized and the receptors immunoprecipitated, e.g., with an antireceptor antibody, as described herein. The immune complexes then are segregated, washed, separated by gel electrophoresis using standard procedures and transferred to a membrane for Western blot analysis using standard procedures. Phosphorylation of the receptor then can be visualized by imnmunodetection with a suitable antibody (e.g., antiphosphoserine, antiphosphothreonine or antiphosphotyrosine), as described above. The bound antibody (e.g., bound antiphosphoserine, antiphosphothreonine or antiphosphotyrosine) then can be detected with $^{125}$I labeled protein A, followed by autoradiography. The amount of phosphorylated receptor detected is anticipated to be significantly greater (5–20 fold increase) in receptors incubated with ligand than receptors exposed to ATP in the absence of ligand.

Ligand-induced receptor phosphorylation of exogenous substrates similarly can be assayed essentially using the methodology described herein. Here, a suitable substrate (e.g., a synthetic polypeptide containing serine, threonine or tyrosine amino acids) is provided to the receptor following ligand exposure and prior to incubation with ATP. The substrate subsequently can be segregated by immunoprecipitation with an antibody specific for the substrate, and phosphorylation detected as described above. As for autophosphorylation, the amount of phosphorylated substrate detected following ligand incubation is anticipated to be greater than that detected for substrates exposed to receptors in the absence of ligand.

EXAMPLE 6

Chimeric Receptor Molecules

Chimeric receptor molecules, e.g., comprising an ALK or ALK analog extracellular and transmembrane region and, for example, part or all of an intracellular domain from another, different receptor or an intracellular domain from a different cell surface molecule, may be constructed using standard recombinant DNA technology and/or an automated DNA synthesizer to construct the desired sequence. As will be appreciated by persons skilled in the art, useful junctions include sequences within the transmembrane region and/or sequences at the junction of either the intracellular or the extracellular domains. Also envisioned are chimers where the extracellular domain or the intracellular domains themselves are chimeric sequences.

Chimeric sequences are envisioned to be particularly useful in screening assays to determine candidate binding ligands (e.g., OP-1 analogs, see below), where the non-receptor intracellular domain provides a suitable second messenger response system that is easy to detect. Potentially useful other second messenger response systems include those which, when activated, induce phosphoinositide hydrolysis, adenylate cyclase, guanylate cyclase or ion channels.

Chimeric receptor molecules have particular utility in gene therapy protocols. For example, a population of cells expressing a chimeric morphogen receptor molecule on their surface and competent for expressing a desired phenotype can be implanted in a mammal at a particular tissue locus. By careful choice of the ligand binding domain used on these receptors a physician can administer to the individual a morphogen agonist capable of: (1) binding to the chimeric receptor alone and (2) stimulating the proliferation and/or differentiation of the implanted cells without affecting endogenous cell populations.

EXAMPLE 7

Considerations for Identifying Other OP-1 Specific Receptors In Nucleic Acid Libraries Identification of ALK-1 allows one to identify other ALK-1 related morphogen receptor sequences in different species as well as in different tissues. ALK-1 sequences themselves can be used as a probe or the sequence may be modified to account for other potential codon usage (e.g., human codon bias.) Currently preferred probe sequences are those which encode the receptor's extracellular domain.

Probes based on the nucleic acid sequence of Seq. ID No. 1 can be synthesized on commercially available DNA synthesizers, e.g. Applied Biosystems model 381A, using standard techniques, e.g. Gait, *Oligonucleotide Synthesis: A Practical Approach,* IRL Press, Washington D.C., 1984). It is preferable that the probes are at least 8–50 bases long, more preferably 18–30 bases long. Probes can be labeled in a variety of ways standard in the art, e.g using radioactive, enzymatic or colormetric labels as described, for example, by Berent et al., (May/June 1985) *Biotechniques:* 208–220; and Jablonski et al., (1986) *Nucleic Acids Research* 14: 6115–6128.

Preferably, low stringency conditions are employed when screening a library for morphogen receptor sequences using a probe derived from OP-1-binding receptor. Preferred ALK-specific probes are those corresponding to bases encoding the extracellular domain ("ECD"), or encoding a unique (nonhomologous) sequence within the cytoplasmic domain. Useful probes may be designed from bases encoding the juxtamembrane region, for example. The probe may be further modified to use a preferred species codon bias. Alternatively, probes derived from the serine/threonine kinase domain can be used to identify new members of the receptor kinase family which can be screened for OP-1 binding using the methods described in Example 8.

For example, for a probe of about 20–40 bases a typical prehybridization, hybridization, and wash protocol is as follows: (1) prehybridization: incubate nitrocellulose filters containing the denatured target DNA for 3–4 hours at 55° C. in 5×Denhardt's solution, 6×SSC (20×SSC consists of 175 g NaCl, 88.2 g sodium citrate in 800 ml $H_2O$ adjusted to pH. 7.0 with 10N NaOH), 0.1% SDS, and 100 mg/ml denatured salmon sperm DNA, (2) hybridization: incubate filters in prehybridization solution plus probe at 42° C. for 14–48 hours, (3) wash; three 15 minutes washes in 6×SSC and 0.1% SDS at room temperature, followed by a final 1–1.5 minute wash in 6×SSC and 0.1% SDS at 55° C. Other equivalent procedures, e.g. employing organic solvents such as formamide, are well known in the art.

Alternatively, morphogen receptor-specific DNA can be amplified using a standard PCR (polymerase chain reaction) methodology such as the one disclosed herein, to amplify approximately 500 base pair fragments. As for the hybridization screening probes described above, the primer sequences preferably are derived from conserved sequences in the serine/threonine kinase domain. Examples of useful PCR amplifications are disclosed in ten Dijke, et al. (1993) *Oncogene* 8: 2879–2887 and (1994) *Science* 264: 101–104, and which also describe the isolation protocols for ALK-1.

7.1 Tissue Distribution of Morphogen Receptors

Determining the tissue distribution of OP-1-specific receptors can be used to identify tissue and cell sources which express these receptors, to identify new, related OP-1-specific receptor molecules, as well as to identify target tissues for OP-1-receptor interactions under naturally occurring conditions. The OP-1 specific receptor molecules (or their mRNA transcripts) readily are identified in different tissues using standard methodologies and minor modifications thereof in tissues where expression may be low. For example, protein distribution can be determined using standard Western blot analysis or immunohistological detection techniques, and antibodies specific to the morphogen receptor molecules of interest. Similarly, the distribution of morphogen receptor transcripts can be determined using standard Northern hybridization protocols and transcript-specific probes or by in situ hybridization.

Any probe capable of hybridizing specifically to a transcript, and distinguishing the transcript of interest from other related transcripts can be used. Because the morphogen receptors described herein likely share high sequence homology in their intracellular domains, the tissue distribution of a specific morphogen receptor transcript may best be determined using a probe specific for the extracellular domain of the molecule. For example, a particularly useful ALK-specific probe sequence is one derived from a unique portion of the 5' coding sequence, the sequence corresponding to the juxtamembrane region, or the 5' or 3' noncoding sequences. The chosen fragment then is labeled using standard means well known and described in the art and herein.

Using these receptor-specific probes, which can be synthetically engineered or obtained from cloned sequences, receptor transcripts can be identified and localized in various tissues of various organisms, using standard methodologies well known to those having ordinary skill in the art. A detailed description of a suitable hybridization protocol is described in Ozkaynak, et al., (1991) *Biochem. Biophys. Res. Comm.* 179: 116–123, and Ozkaynak, et al. (1992) *J Biol. Chem.* 267: 25220–25227. Briefly, total RNA is prepared from various tissues (e.g., murine embryo and developing and adult liver, kidney, testis, heart, brain, thymus, stomach) by a standard methodologies such as by the method of Chomczynski et al. ((1987) *Anal. Biochem* 162: 156–159) and described below. Poly(A)$^+$RNA is prepared by using oligo (dT)-cellulose chromatography (e.g., Type 7, from Pharmacia LKB Biotechnology, Inc.). Poly(A)$^+$RNA (generally 15 mg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5×Denhardts, 5×SSPE, and 0.1% SDS. Following hybridization, the non-specific counts are washed off the filters in 0.1×SSPE, 0.1% SDS at 50° C.

EXAMPLE 8

Demonstration that ALK-1 Is An OP-1-Binding Receptor

Experimental Procedures
Cell Culture

A chondrogenic cell line, ATDC5 (Atsumi et al., 1990 *Cell Dif. Div.* 30: 109–116) was cultured in a 1:1 mixture of Dulbecco's modified Eagle's medium (DMEM) and Ham's F12 containing 5% fetal bovine serum, 10 μg/mi bovine insulin (Sigma Co., Cincinnati) and 100 units/ml penicillin. Cells from a chemically-mutagenized Mv1 Lu cell line (R mutant, clone 4-2 (R4-2)) (Laiho et al., 1990 *J Biol. Chem.* 285: 18518–18524) also were used. R4-2cells were cultured in DMEM containing 10% FBS and 100 units/ml penicillin in 5% C0$_2$ atmosphere at 37° C.

Preparation of Polyclonal Antibodies

Antisera against ALK-1 to -6 were made against synthetic peptides corresponding to the intracellular juxtamembrane parts of the receptors as described herein.

Stable Transfection of CDNA

Stable expression plasmids of human ALK-1, ALK-3 (also referred to in the art as BMPR-1A) and ALK-5 (also referred to in the art as TβR-1) were generated by subcloning the corresponding full length cDNA into pMEP4 (Wrana et al., 1992, *Cell* 71: 1003–1014), a Zn$^{2+}$-inducible mammalian expression vector, using convenient restriction enzyme sites in the polylinker region of the vector. To generate stable transfectants, R4-2cells were transfected with 10 μg each of plasmids by a calcium phosphate precipitation method using a mammalian transfection kit (Stratagene, La Jolla) as described by the manufacturer. After 2 days, selection was initiated by adding 120 U/ml hygromycin B (Wako Chemicals) to the culture medium. Independent colonies were cloned, and after screening by immunoprecipitation following the metabolic labeling of the cells, positive clones were chosen and further analyzed. More than two positive clones for each of the transfectants were subjected to the following experiments, in which no significant difference between independent clones was observed in the magnitude of receptor expression and response to the ligands.

Recombinant Proteins and Radioiodination

Recombinant human TGF-β1 and recombinant human activin A were obtained from H. Ohashi (Kirin Brewery Company Ltd.) and Y. Eto (Ajinomoto Company, Inc.), respectively. Recombinant human OP-1 was obtained as described (Sampath et al., 1992). Iodination of OP-1 was performed according to the chloramine T method as described (ten Dijke et al., (1994) *J Biol. Chem.* 269: 16985–16988).

Metabolic Labeling and Immunoprecipitation

Metabolic labeling of stably transfected R4-2cells was performed for 5 h in methionine- and cysteine-free DMEM with 100 μCi/mi of [$^{35}$S]methionine and [$^{35}$S]cysteine (Promix cell labeling mix; Amersham) in the presence or absence of 100 μM ZnCl$_2$. After labeling, the cells were washed in phosphate-buffered saline and lysed in 1 ml of 20 mM Tris-HCl, pH 7.5, 150 mM NaCl, 10 mM EDTA, 1% Triton X-100, 1% sodium deoxycholate, 1.5% Trasylol (Bayer) and 1 mM phenylmethylsulfonyl fluoride (Sigma). The cell lysates were centrifuged, and supernatants were subjected to immunoprecipitation as previously described (Ichijo, et al., (1993) *J Biol. Chem.* 268: 14505–14513). Briefly, the metabolically labeled lysates were incubated with the antisera against each of ALKs for 45 min at 4° C. Immune complexes were bound to protein A-Sepharose (Kabi-Pharmacia) for 30 min at 4° C., washed four times with a buffer containing 20 mM Tris-HCl, pH 7.5, 500 mM NaCl, 1% Triton X-100, 1% deoxycholate, 0.2% sodium dodecyl sulfate (SDS), followed by one wash in distilled water. The immune complexes were eluted by boiling for 5 min in SDS-sample buffer (100 mM Tris-HCl, pH 8.8, 0.01% bromophenol blue, 36% glycerol, 4% SDS) containing 10 mM dithiothreitol and analyzed by 8.5% SDS-gel electrophoresis. The gel was fixed, dried and subjected to the analysis using a Fuji BAS 2000 Bio-Imaging Analyzer (Fuji Photo Film).

Binding, Affinity Cross-Linking and Immunoprecipitation

For receptor affinity labeling, ATDC5 cells were incubated on ice for 3 h with 300 μM of $^{125}$I-OP-1 in the presence or absence of 15 nM unlabeled OP-1 in the binding buffer (phosphate-buffered saline containing 0.9 mM CaCl$_2$, 0.49 mM MgCl$_2$ and 1 mg/ml bovine serum albumin). For the ALK-transfected R4-2cells, binding was allowed after overnight culture of the cells in the presence and absence of 100 μm ZnCl$_2$. After binding, cells were washed 3 times with the binding buffer and once with phosphate-buffered saline, and crosslinking was performed in the phosphate-buffered saline containing 0.28 mM of disuccinimidyl suberate (DSS; Pierce Chemical Co.) and/or 0.5 mM of Bis (sulfosuccinimidyl) suberate (BS3; Pierce) for 15 min on ice. Cells were washed once with the buffer containing 10 mM Tris-HCl, pH 7.4, 1 mM EDTA and 10% glycerol. Cell lysates were collected after incubation of the cells with 10 mM Tris-HCl pH 7.8, 1% NP-40, 0.15M NaCl, 1 mM EDTA and 1.5% Trasylol for 20 min, and the supernatants were analyzed by SDS-gel electrophoresis under reducing conditions or further subjected to immunoprecipitation. Immunoprecipitation of the labeled complex was done as described above. The immune complexes were eluted by boiling for 5 min in the SDS-sample buffer with 10 mM dithiothreitol, and analyzed using 7 or 8.5% polyacrylamide, followed by analysis using Bio-Imaging Analyzer.

PAI-1 Assay

PAI-1 assay was performed as described previously (Ohtsuki and Massague, (1992) *Mol. Cell. Biol.* 12: 261–265) with minor modifications. In brief, cells were seeded in 6-well cell culture plates and incubated with 100 µM $ZnCl_2$ overnight. The cells were exposed to OP-1, TGF-β1 or activin A in serum-free DMEM without methionine and cysteine for 2 h. Thereafter, cultures were labeled with 30 µCi/ml of [$^{35}$S]methionine and [$^{35}$S]cysteine mixture for 2 h. The cells were removed by washing on ice once in phosphate-buffered saline, four times in 10 mM Tris-HCl, pH 8.0, 0.5% sodium deoxycholate and 1 mM phenylmethylsulphonyl fluoride, two times in 2 mM Tris-HCl, pH 8.0, and once in phosphate-buffered saline. Extracellular-matrix proteins were scraped off and extracted into SDS-sample buffer containing 10 mM dithiothreitol and analyzed by 10% SDS polyacrylamide gel electrophoresis, followed by analysis using Bio-imaging Analyzer. PAI-1 was identified as a 44 to 46 kDa doublet.

$^3$H-Thymidine incorporation Assay

Cells were seeded in 24-well cell culture plates at a density of 104 cells per well in DMEM with 10% FBS, and incubated overnight. The medium was changed to DMEM containing 0.2% FBS and 100 µM $ZnCl_2$, and the cells were incubated for 5 h. The medium was then changed to fresh DMEM containing 0.2% FBS, 100 µM $ZnCl_2$ and various concentrations of OP-1 or TGF-β1. After 16 h of incubation, 0.25 µCi of $^3$H-thymidine (Amersham) was added and the cells were incubated for an additional 2 h. Thereafter, the cells were fixed in 10% trichloroacetic acid for more than 15 min on ice, and solubilized with 1M NaOH. The cell extracts were neutralized with 1M HCl and $^3$H radioactivity was determined in a liquid scintillation counter.

Identification of OP-1 Receptors in an OP-1 Responsive Cell Line.

To identify the signaling receptor(s) for OP-1, we first attempted to find cells were identified which respond to OP-1. The mouse chondrogenic cell line ATDC5 was found to respond well to OP-1 and its proliferation and by alkaline phosphates activity were strongly stimulated. When the ATDC5 cells were analyzed for the binding of $^{125}$I-OP-1 followed by affinity cross-linking and SDS polyacrylamide gel electrophoresis under reducing conditions, $^{125}$I-OP-1 formed three major crosslinked complexes of 50–60 kDa, 70–85 kDa and 95–110 kDa which were effectively competed for binding in the presence of excess unlabeled OP-1. The size of the 70–85 and 95–110 complexes were similar to those of the type I and type II receptor complexes for TGF-β and activin (ten Dijke et al., (1994) *Science* 264: 101–104). The 50–60 kDa component may be a degradation product of a larger complex. In order to exclude the background and to investigate whether certain ALKs may serve as type I receptors for OP-1 in this particular cell line, the cross-linked complexes were further analyzed by immunoprecipitating these complexes using antisera against ALK-1 to ALK-6. Cross-linked complexes of 70–90 kDa could be precipitated by antisera to ALK-1 and ALK-3/BMPR-IA but not by others (e.g., ALK-2, -4, -5, -6), indicating that ALK-1 as well as ALK-3/BMPR-IA form part of the isolated complexes and are competent to bind OP-1. ALK-1 may act as an endogenous Type I receptor for OP-1 or an OP-1-related protein.

Expression and OP-1 Binding of ALKs in Stably Transfected R 4-2 Cells.

Cells of a highly transfectable mink lung epithelial mutant cell line, R4-2, which lack endogenous type I receptor for TGF-β. Were stably transfected with the ALK-1, ALK-3/BMPR-IA and ALK-5/TβR-I cDNAs under the control of $Zn^+$-inducible metallothionein promoter in an expression vector pMEP4. The R4-2transfectants were metabolically labeled with [$^{35}$S]methionine and [$^{35}$S]cysteine in the presence or absence of 100 µM $ZnCl_2$, and the labeled proteins were immunoprecipitated by the antisera against each of ALKs. Labeled components of 50–65 kDa which fit with the sizes predicted from each of ALK cDNA sequences were specifically immunoprecipitated only in the presence of $ZnCl_2$. A broad migration pattern of the components on the gel likely represents heterogenous glycosylation and/or phosphorylation.

In order to investigate whether ALK-1 and ALK-3/BMPR-IA can bind OP-1 when they were expressed in R4-2cells, binding of $^{125}$I-OP-1 was analyzed by affinity cross-linking followed by immunoprecipitation to eliminate the background. When ALK-1 or ALK-3/BMPR-IA was induced by $ZnCl_2$, $^{125}$I-OP-1 bound to ALK-3/BMPR-IA, and to a lesser extent ALK-1, and the cross-linked complexes of 70–95 kDa were precipitated by the respective antisera. Intensity of the band for ALK-1 was weak, however, no cross-linked complex was detected in cells without $Zn^2$+induction, or in ALK-5/TβR-1 expressing cells. When TGF-β1 was used as a radiolabeled ligand, only ALK-5f/βR-1 but not ALK-1 or ALK-3/BMPR-IA formed cross-inked complex with $^{125}$I-TGF-β1. These results indicate that OP-1 and/or OP-1 related proteins can bind ALK-1 and ALK-3 when they are expressed in R4-2cells. The results are presented in Table I below. Binding was specific as determined by standard competition assays. The values represented by "+/−", "+", "++", "+++", and "−" are all qualitative descriptors of the relative amount of radioactivity measured when the crosslinked molecules were gel electrophoresed and subjected to autoradiography. More radioactivity measured indicates a stronger binding interaction detected. In the Table the strength of binding interaction is as follows: +++>++>+>+/−>−.

TABLE I

|   | $^{125}$I-OP-1 | $^{125}$I-TGF-β |
|---|---|---|
| ALK-1 | + | − |
| ALK-3 | ++ | ++ |
| ALK-5 | − | − |

OP-1 Signals through ALK-1 and ALK-3/BMPR-IA

To investigate whether ALK-1 and ALK-3/BMPR-IA transduce any signals upon binding of OP-1, their abilities were determined to mediate signals for extracellular matrix production and cell growth production of PAI-1 was tested using the stable transfectants (FIG. 1). Production of PAI-1 in response to the stimulation by OP-1 in ALK-5/TβR-1 transfected cells was not detected. However, in ALK-1 and ALK-3/BMPR-IA -transfected cells, TGF-β1 and activin had no detectable effects on PAI-1 production, whereas OP-1 dramatically induced the PAI-1 protein in those cells in a $ZnCl_2$ dependent manner. These results indicate that ALK-1 and ALK-3/BMPR-IA can signal an extracellular matrix production response upon binding of OP-1.

Figure 2B:
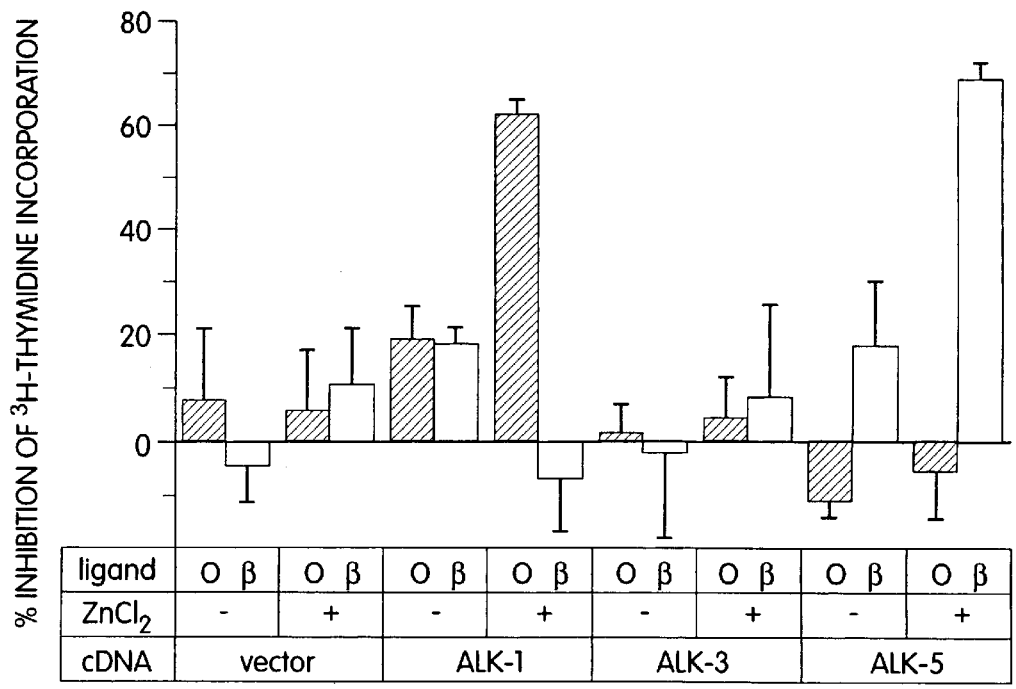
FIG. 2B is a graphic representation of $^3$H-thymidine incorporation in response to OP-1 or TGF-β in cells transfected with ALK-1, ALK-3 or ALK-5.

$^3$H-thymidine incorporation assays were performed to investigate the ability of the three type I receptors ALK-1, ALK-3, ALK-5 to confer growth responsiveness to OP-1. When ALKs were induced in the presence of $ZnCl_2$, R4-2cells expressing ALK-1 were found to respond to OP-1, and their growth was inhibited in a dose dependent manner (FIG. 2A). In contrast, OP-1 had no detectable effect on the cells expressing ALK-3/BMPR-IA or ALK-5/TβR-1 (FIG. 2A). In addition, the growth inhibitory effect of OP-1 on the ALK-1 transfected cells were dependent on the expression of ALK-1 since no inhibition of $^3$H-thymidine incorporation was observed in the absence of $ZnCl_2$. (FIG. 2B). Under these conditions TGF-β only inhibited cell growth in ALK-5 transfected cells.

The experimental results indicate that OP-1 binds ALK-1. The relatively weaker labeling intensity of ALK-1 by $^{125}$I-OP-1 as compared with ALK-3 in ATDC5 cells and transfected R4-2cells could be ascribed to reduced cross-linking efficiency with OP-1 since ALK-1 has fewer lysine residues in its extracellular domain (2 or 3, in human and mouse, respectively) than ALK-3 (7 lysines). Alternatively, the presence of a Type II receptor could be required for tight complex formation; and/or an OP-1 related protein could bind with higher affinity.

OP-1 has been shown to suppress cell proliferation and stimulate the expression of matrix proteins in rat osteosarcoma cells (Maliakal et al., 1994, *Growth Factors* 11: 227–234). The data presented herein demonstrates that ALK-1 is competent to mediate growth-related signals in response to OP-1.

EXAMPLE 9

OP-1, OP-1-Specific Receptor Analog Screening Assays

The present invention is useful to determine whether a ligand, such as a known or putative drug, is capable of binding to and/or activating an OP-1-specific cell surface receptor as described herein. Ligands capable of specific binding interaction with a given OP-1-specific receptor (e.g., ALK-2, ALK-3, ALK-6) are referred to herein as OP-1 analogs and can be used for therapeutic and diagnostic applications. Some analogs will have the ability to stimulate morphogenic activity in the cell, mimicking both the receptor binding and signal transducing activity of OP-1. These are referred to OP-1 agonists or mimetics. Others will have strong binding affinity but will not stimulate morphogenesis, these are OP-1 antagonists. The analogs can be amino acid-based, or they can be composed of non-proteinaceous chemical structures.

The methods and kits described below similarly can be used to identify OP-1-specific receptor analogs, capable of mimicking the binding affinity of ALK-2, ALK-3 or ALK-6 for OP-1. The analogs can be provided to a mammal to interact with serum-soluble OP-1, effectively sequestering the protein and modulating its availability for cell surface interaction.

Transfection of an isolated clone encoding a morphogen receptor into the cell systems described above provides an assay system for the ability of ligands to bind to and/or to activate the receptor encoded by the isolated DNA molecule. Transfection systems, such as those described above, are useful as living cell cultures for competitive binding assays between known or candidate drugs and ligands which bind to the receptor and compete with the binding of known morphogens, which are labeled by radioactive, enzymatic, spectroscopic or other reagents. Membrane preparations containing the receptor and isolated from transfected cells are also useful in these competitive binding assays. Alternatively, and currently preferred, purified receptor molecules or their ligand binding extracellular domains can be plated onto a microtiter well surface, in a modification of a sandwich assay, e.g., as a competition assay, such as an RIA, described above. Finally, as described above, solution assays, and using only the receptor extracellular domain, also may be used to advantage in these assays. Functional assays of second messenger systems or their sequelae in transfection systems act as assays for binding affinity and efficacy in the activation of receptor function or efficacy in the antagonism of receptor function. Such a transfection system constitutes a "drug discovery system", useful for the identification of natural or synthetic compounds with potential for drug development that can be further modified or used directly as therapeutic compounds to activate or inhibit the natural functions of the receptor encoded by the isolated DNA molecule.

Once such candidate drugs (e.g., OP-1 or receptor-binding analogs thereof) are identified, they can be produced in reasonable, useful quantities using standard methodologies known in the art. Amino acid-based molecules can be encoded by synthetic nucleic acid molecules, and expressed in a recombinant expression system as described herein above or in the art. Alternatively, such molecules can be chemically synthesized, e.g., by means of an automated peptide synthesizer, for example. Non-amino acid-based molecules can be produced by standard organic chemical synthesis procedures. Where the candidate molecule is of undetermined structure, or composition, its composition readily can be determined by, for example, mass spectroscopy. Two approaches to identifying analogs typically are practiced in the art: high flux screens and rational design of ligand mimetics. High flux screens typically screen naturally sourced materials or chemical banks for their ability to bind a protein of interest, here, e.g., the receptor. Typically, compounds are obtained from a range of sources, e.g., chemical banks, microbial broths, plant and animal extracts, and the like. In a high flux screen typically, purified receptor, preferably the soluble, ligand binding extracellular domain, is plated onto a microtiter well surface and a standard volume of a sample solution to be tested then is added. Also added is a standard volume having a known quantity of a purified ligand known to bind the receptor with specificity. Preferably the ligand is labeled with a substance that is readily detectable by automated means (e.g., radiolabel, chromophoric, fluorometric, enzymatic or spectroscopic label). The wells then are washed and the amount of label remaining after washing or the amount of label remaining associated with the receptor then is detected. Positive scores are identified by the ability of the test substance to prevent interaction of the labeled ligand with the receptor. The screening assays can be performed without undue experimentation, using standard molecular and cell biology tools in common use in the art. For example, screening assays can be performed in standard 96-well plates. Fifteen such plates reasonably can be set up at a time to perform multiple screening assays in parallel. Thus, with only 10–11 reiterations of the screening assay 15,625 (56) compounds can be screened for their binding affinity. Even allowing for a maximum incubation time of 2 hours, all 15,625 compounds reasonably can be assayed in a matter of days.

High flux screens exploit both the high degree of specificity of the labeled ligand for its receptor, as well as high throughput capacity of computer driven robotics and computer handling of data. Candidate analogs identified in this manner, then can be analyzed structurally and this information used to design and to synthesize analogs having enhanced potency, increased duration of action, increased selectivity and reduced side effects. Candidates also can be used in a rational design program as described below. Finally, candidate analogs also can be tested to determine morphogenic effect, if any, as described below.

The second approach to the identification of analogs uses a rational design approach to create molecules capable of mimicking the binding effect of OP-1 with an OP-1-specific receptor. Here the relevant structure for receptor binding is analyzed to identify critical sequences and structures necessary for binding activity and this information can be used to design and synthesize minimal size morphogen analogs. As for candidate compounds in the high flux assay, design candidates can be tested for receptor binding activity as described above. As described above, a candidate sequence can be further modified by, for example standard biological or chemical mutagenesis techniques to create a candidate derivative having, for example, enhanced binding affinity or another preferred characteristic.

Antibodies capable of interacting specifically with the receptor and competing with OP-1 binding can also be used as an analog. Antibodies can be generated as described above.

OP-1 analogs may be evaluated for their ability to mimic OP-1 or to inhibit OP-1 binding (e.g., agonists or antagonists) by monitoring the effect of the analogs on cells bearing an OP-1-specific receptor (e.g., ALK-1). OP-1 agonists are anticipated to have utility in any application where tissue morphogenesis is desired, such as in the regeneration of damaged tissue resulting from mechanical or chemical trauma, degenerative diseases, tissue destruction resulting from chronic inflammation, cirrhosis, inflammatory diseases, cancer and the like, and in the regeneration of tissues, organs and limbs. OP-1 antagonists are envisioned to have utility in applications where tissue morphogenesis is to be limited as, for example, in the treatment of malignant transformations including, but not limited to, osteosarcomas and Paget's disease.

Several exemplary systems for assaying the ability of a candidate analog transduce an OP-1 -specific signal across the cellular membrane are described below.

9.1 Induction of Osteoblast Differentiation Markers

For example, OP-1 is known to preferentially induce differentiation of progenitor cells, including embryonic mesenchymal cells and primary osteoblasts (see, for example, PCT US92/07432) As one example, OP-1 analogs can be tested for their ability to induce differentiation of primary osteoblasts, by measuring the ability of these analogs to induce production of alkaline phosphatase, PTH-mediated cAMP and osteocalcin, all of which are induced when primary osteoblasts are exposed to OP-1, 60A or dpp.

Briefly, the assays may be performed as follows. In this and all examples involving osteoblast cultures, rat osteoblast-enriched primary cultures preferably are used. Although these cultures are heterogeneous in that the individual cells are at different stages of differentiation, these cultures are believed to more accurately reflect the metabolism and function of osteoblasts in vivo than osteoblast cultures obtained from established cell lines. Unless otherwise indicated, all chemicals referenced are standard, commercially available reagents, readily available from a number of sources, including Sigma Chemical, Co., St. Louis; Calbiochem, Corp., San Diego and Aldrich Chemical Co., Milwaukee.

Rat osteoblast-enriched primary cultures are prepared by sequential collagenase digestion of newborn suture-free rat calvaria (e.g., from 1–2 day-old animals, Long-Evans strain, Charles River Laboratories, Wilmington, Mass.), following standard procedures, such as are described, for example, in Wong et al., (1975) *PNAS* 72: 3167–3171. Rat osteoblast single cell suspensions then are plated onto a multi-well plate (e.g., a 24 well plate) at a concentration of 50,000 osteoblasts per well in alpha MEM (modified Eagle's medium, Gibco, Inc., Long Island) containing 10% FBS (fetal bovine serum), L-glutamine and penicillin/streptomycin. The cells are incubated for 24 hours at 37° C., at which time the growth medium is replaced with alpha MEM containing 1% FBS and the cells incubated for an additional 24 hours so that the cells are in serum-deprived growth medium at the time of the experiment.

Alkaline Phosphatase Induction of Osteoblasts

The cultured cells in serum-free medium are incubated with OP-1, OP-1 analog or a negative control, using a range of concentrations. For example, 0.1, 1.0, 10.0, 40.0 or 80.0 ng OP-1/ml medium typically are used. 72 hours after the incubation period the cell layer is extracted with 0.5 ml of 1% Triton X-100. The resultant cell extract then, is centrifuged, and 100 ml of the extract is added to 90 ml of paranitrosophenylphospate (PNPP)/glycerine mixture and incubated for 30 minutes in a 37° C. water bath and the reaction stopped with 100 ml NaOH. The samples then are run through a plate reader (e.g., Dynatech MR700 plate reader, and absorbance measured at 400 nm, using p-nitrophenol as a standard) to determine the presence and amount of alkaline phosphate activity. Protein concentrations are determined by the Biorad method. Alkaline phosphatase activity is calculated in units/mg protein, where 1 unit=1 nmol p-nitrophenol liberated/30 minutes at 37° C. OP-1 induces a 5-fold increase in the specific activity of alkaline phosphate by this method. Agonists are expected to have similar induction effects. Antagonists should inhibit or otherwise interfere with OP-1 binding, and diminished alkaline phophatase induction should result when the assay is performed with an antagonist in the presence of a limiting amount of OP-1.

Induction of PTH-Mediated CAMP.

The effect of a morphogen analog on parathyroid hormone-mediated cAMP production in rat osteoblasts in vitro may be demonstrated as follows.

Rat osteoblasts are prepared and cultured in a multiwell plate as described above. The cultured cells then are divided into three groups: (1) wells which receive, for example, 1.0, 10.0 and 40.0 ng OP-1/ml medium); (2) wells which receive the candidate analog at various concentration ranges; and (3) a control group which receives no additional factors. The plate is then incubated for another 72 hours. At the end of the 72 hours the cells are treated with medium containing 0.5% bovine serum albumin (BSA) and 1 mM 3-isobutyl-1-methylxanthine for 20 minutes followed by the addition into half of the wells of human recombinant parathyroid hormone (HPTH, Sigma, St. Louis) at a concentration of 200 ng/ml for 10 minutes. The cell layer then is extracted from each well with 0.5 ml of 1% Triton X-100. The cAMP levels then are determined using a radioimmunoassay kit (e.g., Amersham, Arlington Heights, Ill.). OP-1 doubles cAMP production in the presence of PTH. Agonists are expected to have similar induction effects. Antagonists are expected to inhibit or otherwise interfere with OP-1 binding, and diminished cAMP production should result when the assay is performed with an antagonist in the presence of limiting the amount of OP-1.

Induction of Osteocalcin Production

Osteocalcin is a bone-specific protein synthesized by osteoblasts which plays an integral role in the rate of bone mineralization in vivo. Circulating levels of osteocalcin in serum are used as a marker for osteoblast activity and bone formation in vivo. Induction of osteocalcin synthesis in osteoblast-enriched cultures can be used to demonstrate morphogenic efficacy in vitro.

Rat osteoblasts are prepared and cultured in a multi-well plate as above. In this experiment the medium is supplemented with 10% FBS, and on day 2, cells are fed with fresh medium supplemented with fresh 10 mM b-glycerophosphate (Sigma, Inc.). Beginning on day 5 and twice weekly thereafter, cells are fed with a complete mineralization medium containing all of the above components plus fresh L(+)-ascorbate, at a final concentration of 50 mg/ml medium. OP-1 or OP-1 analog then is added to the wells directly, e.g., in 50% acetonitrile (or 50% ethanol) containing 0.1% trifluoroacetic acid (TFA), at no more than 5 ml OP-1/ml medium. Control wells receive solvent vehicle only. The cells then are re-fed and the conditioned medium sample diluted 1:1 in standard radioimmunoassay buffer containing standard protease inhibitors and stored at $-20°$ C. until assayed for osteocalcin. Osteocalcin synthesis is measured by standard radioimmunoassay using a commercially available osteocalcin-specific antibody and can be confirmed by Northern blot analysis to calculate the amount of osteocalcin MRNA produced in the presence and absence of OP-1 or OP-1 analog. OP-1 induces a dose-dependent increase in osteocalcin production (5-fold increase using 25 ng of OP-1 protein/ml), and a 20-fold increase in osteocalcin mRNA. Agonists are expected to have similar induction effects; antagonists are expected to inhibit or otherwise interfere with OP-1 binding, thereby substantially interfering with osteocalcin induction in the presence of a limiting amount of OP-1.

Mineralization is determined on long term cultures (13 day) using a modified von Kossa staining technique on fixed cell layers: cells are fixed in fresh 4% paraformaldehyde at $23°$ C. for 10 min, following rinsing cold 0.9% NaCl. Fixed cells then are stained for endogenous alkaline phosphatase at pH 9.5 for 10 min, using a commercially available kit (Sigma, Inc.) Purple stained cells then are dehydrated with methanol and air dried. After 30 min incubation in 3% $AgNO_3$ in the dark, $H_2O$-rinsed samples are exposed for 30 sec to 254 nm WV light to develop the black silver-stained phosphate nodules. Individual mineralized foci (at least 20 mm in size) are counted under a dissecting microscope and expressed as nodules/culture. OP-1 induces a 20-fold increase in initial mineralization rate. Agonists are expected to have similar induction effects; antagonists are expected to inhibit or otherwise interfere with OP-1 binding, thereby inhibiting mineralization induction in the presence of a limiting amount of OP-1.

9.2 Induction of a Constructed Reporter Gene

Alternatively, a reporter gene construct can be used to determine the ability of candidate molecule to induce signal transduction across a membrane following receptor binding. For example, PAI-1 protein, (Plasminogen Activator Inhibitor-1) expression can be induced by OP-1 in Mv1Lu-cells (see above). Also, as demonstrated above, ALK-1, when overexpressed in a chemically mutagenized derivative of these cells, can mediate PAI-1 induction in the presence of OP-1.

Accordingly, PAI-1 promoter elements can be fused to a reporter gene and induction of the reporter gene monitored following incubation of the transfected cell with a candidate analog. As one example, the luciferase reporter gene can be used, in, for example, the construct p3TP-Lux described by Wrana et al. (1992) *Cell* 71: 1003–1014 and Attisano et al (1993) *Cell* 74: 671–680. This reporter gene construct includes a region of the human PAI-i gene promoter in combination with three sets of tetradecanoyl phorbol—acetate responsive elements upstream of the luciferase open reading frame.

In a typical assay, transfected cells starved in DMEM containing 0.1% fetal bovine serum and antibiotics (e.g., 100 units/ml penicillin and 50 $\mu$g/ml streptomycin) for 6 hrs., and then exposed to ligand for 24 hr. Luciferase activity in the cell lysate then is measured using a luminometer in the luciferase assay system, according to the manufacturer's protocol (Promega). In Mv1Lu mutant cells, "R mutant" cells co-transfected with ALK-2 and ActRII, OP-1-mediated induction of luciferase activity.

9.3 Inhibition of Epithelial cell proliferation

OP-1 is known to inhibit epithelial cells. Thus, the ability of a candidate analog to inhibit cell proliferation, as measured by $^3$H-thymidine uptake by an epithelial cell can be used in an assay to evaluate signal transduction activity of the candidate. Analogs competent to inhibit epithelial cell growth are contemplated to have particular utility in therapeutic applications where limitation of a proliferating cell population is desired. Such applications include chemotherapies and radiation therapies where limiting the growth of a normally proliferating population of cells can protect these cells from the cytotoxic effects of these cancer therapies. (see e.g., WO 94/06420). In addition, psoriasis and other tissue disorders resulting from uncontrolled cell proliferation, including benign and malignant neoplasties, can be modulated by use of an OP-1 analog.

As an example, mink lung epithelial cell growth is inhibited by OP-1. (see, PCT US93/08885; WO 94/06420.) As described above, derivatives of these cells [e.g., "R-4 mutants", clone 4-2, Laiho et al. (1990) *J Biol. Chem.* 265: 18518–18524] can be transfected with DNA encoding OP-1-specific receptors and induced to express these receptors. The transfected cells, then can be assayed for a candidate analog's ability to block cell growth. As one example, when R-4 cells are transfected with ALK-1 under a $ZnCl^+$-inducible promoter, and induced to express the receptor following induction with $ZnCl_2$, cell growth can be inhibited in the presence of OP-1 in a dose dependent manner.

In a typical assay, cells are seeded in 24-well cell culture plates at a density of 104 cells per well in DMEM with 10% FBS, and incubated overnight. The medium is replaced with DMEM containing 0.2% FBS and 100 $\mu$M $ZnCl_2$, and the cells are incubated for 5 h, after which the medium is replaced with fresh DMEM containing 0.2% FBS, 100 $\mu$M $ZnCl_2$ and various concentrations of OP-1 or an analog candidate. After 16 h of incubation, 0.25 Ci of $^3$H-thymidine (Amersham) are added and the cells incubated for an additional 2 h. Thereafter, the cells are fixed in 10% trichloroacetic acid for more than 15 min on ice, and solubilized with 1M NaOH. The cell extracts are neutralized with 1M HCl and $^3$H radioactivity determined in a liquid scintillation counter.

EXAMPLE 10

Screening Assay for Compounds Which Alter Endogenou OP-1 Receptor Expression Levels Candidate compound(s) which can be administered to affect the level of a given endogenous OP-1 receptor can be found using the following screening assay, in which the level of OP-1 receptor production by a cell type which produces measurable levels of the receptor is determined by incubating the cell in culture with and without the candidate compound, in order to assess the effects of the compound on the cell. This can also be accomplished by detection of the OP-1 receptor either at the protein level by Western blot or immunolocalization, or at the RNA level by Northern blot or in situ hybridization. The protocol is based on a procedure for identifying compounds which alter endogenous levels of OP-1 expression, a detailed description also may be found in PCT US 92/07359, incorporated herein by reference.

Cell cultures of, for example, bone, brain, intestine, lung, heart, eye, breast, gonads, kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells can be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferring, glucose, albumin, or other growth factors).

Cell samples for testing the level of OP-1 receptor production are collected periodically and evaluated for receptor production by immunoblot analysis (Sambrook et al., eds., 1989, *Molecular Cloning*, Cold Spring Harbor Press, Cold Spring Harbor, N.Y.), or, alternatively, a portion of the cell culture itself can be collected periodically and used to prepare poly(A)$^+$RNA for mRNA analysis by Northern blot analysis. To monitor de novo receptor synthesis, some cultures are labeled according to conventional procedures with an $^{35}$S-methionine/$^{35}$S-cysteine mixture for 6–24 hours and then evaluated to quantitate receptor synthesis by conventional immunoassay methods. Alternatively, anti-receptor antibodies may be labeled and incubated with the cells or cell lysates, and the bound complexes detected and quantitated by conventional means, such as those described hereinabove. Northern blots may be performed using a portion of the OP-1 receptor coding sequence to create hybridization probes, and following the RNA hybridization protocol described herein.

EXAMPLE 11

General Formation/Administration Considerations

The analogs and constructs described herein can be provided to an individual as part of a therapy to enhance, inhibit, or otherwise modulate the in vivo binding interaction between OP-1 and one or more OP-1-specific cell surface receptors. The molecules then comprise part of a pharmaceutical composition as described herein below and can be administered by any suitable means, preferably directly or systemically, e.g., parenterally or orally. Where the therapeutic molecule is to be provided directly (e.g, locally, as by injection, to a desired tissue site), or parenterally, such as by intravenous, subcutaneous, intramuscular, intraorbital, ophthaliic, intraventricular, intracranial, intracapsular, intraspinal, intracisternal, intraperitoneal, buccal, rectal, vaginal, intranasal or by aerosol administration, the therapeutic preferably comprises part of an aqueous solution. The solution preferably is physiologically acceptable so that in addition to delivery of the desired morphogen to the patient, the solution does not otherwise adversely affect the patient's electrolyte and volume balance. The aqueous medium for the therapeutic molecule thus may comprise normal physiologic saline (0.9% NaCl, 0.15M), pH 7–7.4 or other pharmaceutically acceptable salts thereof.

Useful solutions for oral or parenteral administration can be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, can include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the morphogen in vivo.

Other potentially useful parenteral delivery systems for these therapeutic molecules include ethylene-vinyl acetate copolymer particles, osmotic pumps, implantable infusion systems, and liposomes. Formulations for inhalation administration may contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally.

Alternatively, the morphogens described herein may be administered orally.

The therapeutic molecules can also be associated with means for targeting the therapeutic to a desired tissue. For example, tetracycline and diphosphonates (bisphosphonates) are known to bind to bone mineral, particularly at zones of bone remodeling, when they are provided systemically in a mammal. Accordingly, these molecules may be included as useful agents for targeting therapeutics to bone tissue. Alternatively, an antibody or other binding protein that interacts specifically with a surface molecule on the desired target tissue cells can also be used. Such targeting molecules further can be covalently associated to the therapeutic molecule e.g., by chemical crosslinking, or by using standard genetic engineering means to create, for example, an acid labile bond such as an Asp-Pro linkage. Useful targeting molecules can be designed, for example, using the single chain binding site technology disclosed, for example, in U.S. Pat. No. 5,091, 513.

Finally, therapeutic molecules can be administered alone or in combination with other molecules known to have a beneficial effect on tissue morphogenesis, including molecules capable of tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration can include nerve growth factors. Other useful cofactors include symptom-alleviating cofactors, including antiseptics, antibiotics, antiviral and antifungal agents and analgesics and anesthetics.

Therapeutic molecules further can be formulated into pharmaceutical compositions by admixture with pharmaceutically acceptable nontoxic excipients and carriers. As noted above, such compositions can be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition may include the morphogen dispersed in a fibrinogen-thrombin composition or other bioadhesive such as is disclosed, for example in PCT US91/09275, the disclosure of which is incorporated herein by reference. The composition then can be painted, sprayed or otherwise applied to the desired tissue surface.

The compositions can be formulated for parenteral or oral administration to humans or other mammals in therapeutically effective amounts, e.g., amounts which provide appropriate concentrations of the analog to target tissue for a time sufficient to induce the desired effect.

Where the analog is to be used as part of a transplant procedure, it can be provided to the living tissue or organ to be transplanted prior to removal of tissue or organ from the donor. The analog may be provided to the donor host directly, as by injection of a formulation comprising the analog into the tissue, or indirectly, e.g., by oral or parenteral administration, using any of the means described above.

Alternatively or, in addition, once removed from the donor, the organ or living tissue can be placed in a preservation solution containing the therapeutic molecule. In addition, the recipient also preferably is provided with the analog just prior to, or concomitant with, transplantation. In all cases, the analog can be administered directly to the tissue at risk, as by injection to the tissue, or it may be provided systemically, either by oral or parenteral administration, using any of the methods and formulations described herein and/or known in the art.

Where the therapeutic molecule comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution. Generally, an organ preservation solution usually possesses one or more of the following properties: (a) an osmotic pressure substantially equal to that of the inside of a mammalian cell,(solutions typically are hyperosmolar and have $K^+$ and/or $Mg^{2+}$ ions present in an amount sufficient to produce an osmotic pressure slightly higher than the inside of a mammalian cell); (b) the solution typically is capable of maintaining substantially normal ATP levels in the cells; and (c) the solution usually allows optimum maintenance of glucose metabolism in the cells. Organ preservation solutions also may contain anticoagulants, energy sources such as glucose, fructose and other sugars, metabolites, heavy metal chelators, glycerol and other materials of high viscosity to enhance survival at low temperatures, free oxygen radical inhibiting and/or scavenging agents and a pH indicator. A detailed description of preservation solutions and useful components can be found, for example, in U.S. Pat. No. 5,002,965, the disclosure of which is incorporated herein by reference.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of tissue loss or defect, the overall health status of the particular patient, the relative biological efficacy of the compound selected, the formulation of the compound, the presence and types of excipients in the formulation, and the route of administration. In general terms, the therapeutic molecules of this invention may be provided to and individual where typical dose ranges are from about 10 ng/kg to about 1 g/kg of body weight per day; a preferred dose range being from about 0.1 mg/kg to 100 mg/kg of body weight. No obvious morphogen-induced pathological lesions are induced when mature morphogen (e.g., OP-1, 20 mg) is administered daily to normal growing rats for 21 consecutive days. Moreover, 10 mg systemic injections of morphogen (e.g., OP-1) injected daily for 10 days into normal newborn mice does not produce any gross abnormalities.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for identifying an OP-1 analog comprising the steps of:
   (a) exposing a sample comprising cells expressing an ALK-1 receptor having the amino acid sequence of SEQ ID NO: 2 to a candidate OP-1 analog; and
   (b) detecting specific binding of said candidate to said receptor, wherein, the detection of specific binding of said candidate to said receptor identifies said candidate as an OP-1 analog.

2. A method for identifying an OP-1 analog said analog being characterized as having substantially the same binding affinity as OP-1 for a cell surface receptor, the method comprising the steps of:
   (a) exposing a sample comprising cells having an ALK-1 receptor which has the amino acid sequence of SEQ ID NO: 2 that specifically binds a morphogen, to a candidate OP-1 analog;
   (b) detecting induction of an OP-1-mediated cellular response in said sample;

wherein, said induction of an OP-1-mediated cellular response identifies said candidate as an OP-1 analog.

3. The method of claim 1 or 2 wherein said sample further comprises cells having part or all of a Type II serine/threonine kinase receptor having binding affinity for OP-1, activin or BMP-4.

* * * * *